United States Patent
Taylor et al.

(10) Patent No.: US 10,869,687 B2
(45) Date of Patent: *Dec. 22, 2020

(54) TISSUE SEPARATING SYSTEMS AND METHODS

(71) Applicant: The Spectranetics Corporation, Colorado Springs, CO (US)

(72) Inventors: Kevin D. Taylor, Colorado Springs, CO (US); Chris Reiser, Stevenson Ranch, CA (US); Sean Coe, Plymouth, MN (US); Kenneth D. Harlan, Peyton, CO (US); Charles Kennergren, Gothenburg (SE)

(73) Assignee: SPECTRANETICS LLC, Colorado Springs, CO (US)

( * ) Notice: Subject to any disclaimer, the term of this patent is extended or adjusted under 35 U.S.C. 154(b) by 110 days.

This patent is subject to a terminal disclaimer.

(21) Appl. No.: 15/710,187

(22) Filed: Sep. 20, 2017

(65) Prior Publication Data

US 2018/0008301 A1    Jan. 11, 2018

Related U.S. Application Data

(63) Continuation of application No. 14/682,779, filed on Apr. 9, 2015, now Pat. No. 9,801,650, which is a
(Continued)

(51) Int. Cl.
*A61B 17/3205*    (2006.01)
*A61B 17/32*    (2006.01)
(Continued)

(52) U.S. Cl.
CPC .......... *A61B 17/3205* (2013.01); *A61B 1/32* (2013.01); *A61B 17/32002* (2013.01);
(Continued)

(58) Field of Classification Search
CPC .......... A61B 17/32002; A61B 17/3205; A61B 17/32053; A61B 17/320758;
(Continued)

(56) References Cited

U.S. PATENT DOCUMENTS

1,663,761 A    3/1928    Johnson
3,400,708 A    9/1968    Scheidt
(Continued)

FOREIGN PATENT DOCUMENTS

JP    H05506382 A    9/1993
JP    2004516073 A    6/2004
(Continued)

OTHER PUBLICATIONS

U.S. Appl. No. 62/005,315 entitled Surgical Instrument for Removing an Implanted Object filed May 30, 2014.
(Continued)

*Primary Examiner* — Robert A Lynch

(57) ABSTRACT

Systems and methods for separating an object such as a pacing lead from a patient tissue involve a flexible and torqueable shaft having an internal lumen sized to receive the object, and a hard separating mechanism for separating the object from the tissue. Typically the shaft and separating mechanism are advanced along or toward the object, and the separating mechanism is contacted with the tissue. The shaft is rotated to effect separation between the object and the tissue. The systems and methods are well suited for use in cardiac pacing or defibrillator lead explant procedures.

11 Claims, 15 Drawing Sheets

Related U.S. Application Data continuation of application No. 11/615,005, filed on Dec. 22, 2006, now Pat. No. 9,028,520.

(51) Int. Cl.
  *A61N 1/05* (2006.01)
  *A61B 1/32* (2006.01)

(52) U.S. Cl.
  CPC .. *A61N 1/057* (2013.01); *A61B 2017/320044* (2013.01); *A61B 2017/320056* (2013.01); *A61N 2001/0578* (2013.01)

(58) Field of Classification Search
  CPC ....... A61B 2017/320032; A61B 2017/320056; A61B 10/0233; A61B 10/0283; A61N 2001/0578
  See application file for complete search history.

(56) References Cited

U.S. PATENT DOCUMENTS

| | | |
|---|---|---|
| 3,614,953 A | 10/1971 | Moss |
| 4,051,596 A | 10/1977 | Hofmann |
| 4,203,444 A | 5/1980 | Bonnell et al. |
| 4,246,902 A | 1/1981 | Martinez |
| 4,274,414 A | 6/1981 | Johnson et al. |
| 4,471,777 A | 9/1984 | McCorkle, Jr. |
| 4,517,977 A | 5/1985 | Frost |
| 4,582,056 A | 4/1986 | McCorkle et al. |
| 4,587,972 A | 5/1986 | Morantte et al. |
| 4,598,710 A | 7/1986 | Kleinberg et al. |
| 4,646,738 A | 3/1987 | Trott |
| 4,662,869 A | 5/1987 | Wright |
| 4,674,502 A | 6/1987 | Imonti |
| 4,729,763 A | 3/1988 | Henrie |
| 4,754,755 A | 7/1988 | Husted |
| 4,767,403 A | 8/1988 | Hodge |
| 4,790,310 A | 12/1988 | Ginsburg et al. |
| 4,943,289 A | 7/1990 | Goode et al. |
| 4,950,277 A | 8/1990 | Farr |
| 4,988,347 A | 1/1991 | Goode et al. |
| 5,009,659 A | 4/1991 | Hamlin et al. |
| 5,011,482 A | 4/1991 | Goode et al. |
| 5,013,310 A | 5/1991 | Goode et al. |
| 5,031,634 A | 7/1991 | Simon |
| 5,078,723 A | 1/1992 | Dance et al. |
| 5,152,744 A | 10/1992 | Krause et al. |
| 5,201,316 A | 4/1993 | Pomeranz et al. |
| 5,207,683 A | 5/1993 | Goode et al. |
| 5,263,928 A | 11/1993 | Trauthen et al. |
| 5,275,609 A | 1/1994 | Pingleton et al. |
| 5,290,275 A | 3/1994 | Kittrell et al. |
| 5,290,303 A | 3/1994 | Pingleton et al. |
| 5,383,199 A | 1/1995 | Laudenslager et al. |
| 5,395,328 A | 3/1995 | Ockuly et al. |
| 5,423,330 A * | 6/1995 | Lee ................... A61B 10/0233 600/566 |
| 5,456,680 A | 10/1995 | Taylor et al. |
| 5,484,433 A | 1/1996 | Taylor et al. |
| 5,488,958 A * | 2/1996 | Topel ............ A61B 17/320016 600/567 |
| 5,507,751 A | 4/1996 | Goode et al. |
| 5,562,694 A | 10/1996 | Sauer et al. |
| 5,569,284 A | 10/1996 | Young et al. |
| 5,575,797 A | 11/1996 | Neubauer et al. |
| 5,620,451 A | 4/1997 | Rosborough |
| 5,632,749 A | 5/1997 | Goode et al. |
| 5,643,251 A | 7/1997 | Hillsman et al. |
| 5,651,781 A | 7/1997 | Grace |
| 5,697,936 A | 12/1997 | Shipko et al. |
| 5,697,944 A | 12/1997 | Lary |
| 5,718,237 A | 2/1998 | Haaga |
| 5,725,523 A | 3/1998 | Mueller |
| 5,766,164 A | 6/1998 | Mueller et al. |
| 5,782,823 A | 7/1998 | Mueller |
| 5,807,399 A | 9/1998 | Laske et al. |
| 5,814,044 A | 9/1998 | Hooven |
| 5,823,971 A | 10/1998 | Robinson et al. |
| 5,824,026 A | 10/1998 | Diaz |
| 5,836,868 A * | 11/1998 | Ressemann .... A61B 17/320725 606/159 |
| 5,863,294 A | 1/1999 | Alden |
| 5,873,886 A | 2/1999 | Larsen et al. |
| 5,879,365 A | 3/1999 | Whitfield et al. |
| 5,893,862 A | 4/1999 | Pratt et al. |
| 5,899,915 A | 5/1999 | Saadat |
| 5,910,150 A | 6/1999 | Saadat |
| 5,931,848 A | 8/1999 | Saadat |
| 5,941,893 A | 8/1999 | Saadat |
| 5,951,581 A | 9/1999 | Saadat et al. |
| 5,972,012 A | 10/1999 | Ream et al. |
| 5,980,515 A | 11/1999 | Tu |
| 5,980,545 A | 11/1999 | Pacala et al. |
| 6,007,512 A | 12/1999 | Hooven |
| 6,010,476 A | 1/2000 | Saadat |
| 6,019,756 A | 2/2000 | Mueller et al. |
| 6,022,336 A | 2/2000 | Zadno-Azizi et al. |
| 6,027,497 A | 2/2000 | Daniel et al. |
| 6,033,402 A | 3/2000 | Tu et al. |
| 6,036,685 A | 3/2000 | Mueller |
| 6,051,008 A | 4/2000 | Saadat et al. |
| 6,066,131 A | 5/2000 | Mueller et al. |
| 6,080,175 A | 6/2000 | Hogendijk |
| 6,083,237 A | 7/2000 | Huitema et al. |
| 6,099,537 A | 8/2000 | Sugai et al. |
| 6,102,926 A | 8/2000 | Tartaglia et al. |
| 6,120,520 A | 9/2000 | Saadat et al. |
| 6,126,654 A | 10/2000 | Giba et al. |
| 6,136,005 A | 10/2000 | Goode et al. |
| 6,139,543 A | 10/2000 | Esch et al. |
| 6,152,909 A | 11/2000 | Bagaoisan et al. |
| 6,152,918 A | 11/2000 | Padilla et al. |
| 6,156,049 A | 12/2000 | Lovato et al. |
| 6,159,203 A | 12/2000 | Sinofsky |
| 6,159,225 A | 12/2000 | Makower |
| 6,162,214 A | 12/2000 | Mueller et al. |
| 6,165,188 A | 12/2000 | Saadat et al. |
| 6,167,315 A | 12/2000 | Coe et al. |
| 6,174,307 B1 | 1/2001 | Daniel et al. |
| 6,190,352 B1 | 2/2001 | Haarala et al. |
| 6,190,353 B1 | 2/2001 | Makower et al. |
| 6,203,537 B1 | 3/2001 | Adrian |
| 6,210,400 B1 | 4/2001 | Hebert et al. |
| 6,228,076 B1 | 5/2001 | Winston et al. |
| 6,235,044 B1 | 5/2001 | Root et al. |
| 6,241,692 B1 | 6/2001 | Tu et al. |
| 6,245,011 B1 | 6/2001 | Dudda et al. |
| 6,251,121 B1 | 6/2001 | Saadat |
| 6,258,083 B1 | 7/2001 | Daniel et al. |
| 6,290,668 B1 | 9/2001 | Gregory et al. |
| 6,315,774 B1 | 11/2001 | Daniel et al. |
| 6,324,434 B2 | 11/2001 | Coe et al. |
| 6,342,061 B1 * | 1/2002 | Kauker ............ A61B 17/32002 606/180 |
| 6,395,002 B1 | 5/2002 | Ellman et al. |
| 6,398,773 B1 | 6/2002 | Bagaoisan et al. |
| 6,402,771 B1 | 6/2002 | Palmer et al. |
| 6,402,781 B1 | 6/2002 | Langberg et al. |
| 6,419,674 B1 | 7/2002 | Bowser et al. |
| 6,419,684 B1 | 7/2002 | Heisler et al. |
| 6,423,051 B1 | 7/2002 | Kaplan et al. |
| 6,428,539 B1 | 8/2002 | Baxter et al. |
| 6,428,556 B1 | 8/2002 | Chin |
| 6,432,119 B1 | 8/2002 | Saadat |
| 6,436,054 B1 | 8/2002 | Viola et al. |
| 6,436,114 B1 | 8/2002 | Novak et al. |
| 6,454,741 B1 | 9/2002 | Muni et al. |
| 6,454,758 B1 | 9/2002 | Thompson et al. |
| 6,461,349 B1 | 10/2002 | Elbrecht et al. |
| 6,478,777 B1 | 11/2002 | Honeck et al. |
| 6,488,636 B2 | 12/2002 | Bryan et al. |
| 6,500,182 B2 | 12/2002 | Foster |
| 6,512,959 B1 | 1/2003 | Gomperz et al. |
| 6,527,752 B1 | 3/2003 | Bosley et al. |

(56) References Cited

U.S. PATENT DOCUMENTS

| | | |
|---|---|---|
| 6,537,314 B2 | 3/2003 | Langberg et al. |
| 6,554,779 B2 | 4/2003 | Viola et al. |
| 6,558,382 B2 | 5/2003 | Jahns et al. |
| 6,565,588 B1 | 5/2003 | Clement et al. |
| 6,569,082 B1 | 5/2003 | Chin |
| 6,575,997 B1 | 6/2003 | Palmer et al. |
| 6,592,607 B1 | 7/2003 | Palmer et al. |
| 6,595,982 B2 | 7/2003 | Sekino et al. |
| 6,599,296 B1 | 7/2003 | Gillick et al. |
| 6,602,241 B2 | 8/2003 | Makower et al. |
| 6,607,547 B1 | 8/2003 | Chin |
| 6,610,046 B1 | 8/2003 | Usami et al. |
| 6,610,066 B2 | 8/2003 | Dinger et al. |
| 6,613,013 B2 | 9/2003 | Haarala et al. |
| 6,620,153 B2 | 9/2003 | Mueller et al. |
| 6,620,160 B2 | 9/2003 | Lewis et al. |
| 6,620,180 B1 * | 9/2003 | Bays ............... A61B 17/32002 606/171 |
| 6,641,590 B1 | 11/2003 | Palmer et al. |
| 6,652,480 B1 | 11/2003 | Imran et al. |
| 6,652,548 B2 | 11/2003 | Evans et al. |
| 6,660,021 B1 | 12/2003 | Palmer et al. |
| 6,663,626 B2 | 12/2003 | Truckai et al. |
| 6,669,685 B1 | 12/2003 | Rizoiu et al. |
| 6,673,090 B2 | 1/2004 | Root et al. |
| 6,687,548 B2 | 2/2004 | Goode |
| 6,702,813 B1 | 3/2004 | Baxter et al. |
| 6,706,018 B2 | 3/2004 | Westlund et al. |
| 6,706,052 B1 | 3/2004 | Chin |
| 6,706,065 B2 | 3/2004 | Langberg et al. |
| 6,709,456 B2 | 3/2004 | Langberg et al. |
| 6,712,773 B1 | 3/2004 | Viola |
| 6,712,826 B2 | 3/2004 | Lui |
| 6,772,014 B2 | 8/2004 | Coe et al. |
| 6,802,838 B2 | 10/2004 | Loeb et al. |
| 6,805,692 B2 | 10/2004 | Muni et al. |
| 6,810,882 B2 | 11/2004 | Langberg et al. |
| 6,818,001 B2 | 11/2004 | Wulfman et al. |
| 6,860,860 B2 | 3/2005 | Viola |
| 6,871,085 B2 | 3/2005 | Sommer |
| 6,884,240 B1 | 4/2005 | Dykes |
| 6,887,238 B2 | 5/2005 | Jahns et al. |
| 6,893,450 B2 | 5/2005 | Foster |
| 6,913,612 B2 | 7/2005 | Palmer et al. |
| 6,962,585 B2 | 11/2005 | Poleo et al. |
| 6,979,290 B2 | 12/2005 | Mourlas et al. |
| 6,979,319 B2 | 12/2005 | Manning et al. |
| 6,989,028 B2 | 1/2006 | Lashinski et al. |
| 6,999,809 B2 | 2/2006 | Currier et al. |
| 7,004,956 B2 | 2/2006 | Palmer et al. |
| 7,008,434 B2 | 3/2006 | Kurz et al. |
| 7,011,682 B2 | 3/2006 | Lashinski et al. |
| 7,033,335 B2 | 4/2006 | Haarala et al. |
| 7,033,344 B2 | 4/2006 | Imran |
| 7,033,357 B2 | 4/2006 | Baxter et al. |
| 7,060,061 B2 | 6/2006 | Altshuler et al. |
| 7,063,693 B2 | 6/2006 | Guenst |
| 7,077,856 B2 | 7/2006 | Whitman |
| 7,092,765 B2 | 8/2006 | Geske et al. |
| 7,104,983 B2 | 9/2006 | Grasso et al. |
| 7,114,642 B2 | 10/2006 | Whitman |
| 7,117,039 B2 | 10/2006 | Manning et al. |
| 7,149,587 B2 | 12/2006 | Wardle et al. |
| 7,151,965 B2 | 12/2006 | Osypka |
| 7,189,207 B2 | 3/2007 | Viola |
| 7,191,015 B2 | 3/2007 | Lamson et al. |
| 7,192,430 B2 | 3/2007 | Truckai et al. |
| 7,204,824 B2 | 4/2007 | Moulis |
| 7,214,180 B2 | 5/2007 | Chin |
| 7,226,459 B2 | 6/2007 | Cesarini et al. |
| 7,238,179 B2 | 7/2007 | Brucker et al. |
| 7,238,180 B2 | 7/2007 | Mester et al. |
| 7,252,641 B2 | 8/2007 | Thompson et al. |
| 7,264,587 B2 | 9/2007 | Chin |
| 7,273,478 B2 | 9/2007 | Appling et al. |
| 7,276,052 B2 | 10/2007 | Kobayashi et al. |
| 7,288,096 B2 | 10/2007 | Chin |
| 7,296,577 B2 | 11/2007 | Lashinski et al. |
| 7,306,588 B2 | 12/2007 | Loeb et al. |
| 7,326,226 B2 | 2/2008 | Root et al. |
| 7,328,071 B1 | 2/2008 | Stehr et al. |
| 7,344,546 B2 | 3/2008 | Wulfman et al. |
| 7,357,794 B2 | 4/2008 | Makower et al. |
| 7,359,756 B2 | 4/2008 | Goode |
| 7,369,901 B1 | 5/2008 | Morgan et al. |
| 7,392,095 B2 | 6/2008 | Flynn et al. |
| 7,396,354 B2 | 7/2008 | Rychnovsky et al. |
| 7,398,781 B1 | 7/2008 | Chin |
| 7,449,010 B1 | 11/2008 | Hayase et al. |
| 7,462,167 B2 | 12/2008 | Kratz et al. |
| 7,485,127 B2 | 2/2009 | Nistal |
| 7,494,484 B2 | 2/2009 | Beck et al. |
| 7,507,252 B2 | 3/2009 | Lashinski et al. |
| 7,509,169 B2 | 3/2009 | Eigler et al. |
| 7,510,576 B2 | 3/2009 | Langberg et al. |
| 7,513,877 B2 | 4/2009 | Viola |
| 7,513,892 B1 | 4/2009 | Haarala et al. |
| 7,526,342 B2 | 4/2009 | Chin et al. |
| 7,537,602 B2 | 5/2009 | Whitman |
| 7,540,865 B2 | 6/2009 | Griffin et al. |
| 7,544,197 B2 | 6/2009 | Kelsch et al. |
| 7,559,941 B2 | 7/2009 | Zannis et al. |
| D600,792 S | 9/2009 | Eubanks et al. |
| 7,591,790 B2 | 9/2009 | Pflueger |
| 7,597,698 B2 | 10/2009 | Chin |
| 7,606,615 B2 | 10/2009 | Makower et al. |
| 7,611,474 B2 | 11/2009 | Hibner et al. |
| 7,637,904 B2 | 12/2009 | Wingler et al. |
| 7,645,286 B2 | 1/2010 | Catanese et al. |
| 7,648,466 B2 | 1/2010 | Stephens et al. |
| 7,651,503 B1 | 1/2010 | Coe et al. |
| 7,651,504 B2 | 1/2010 | Goode et al. |
| D610,259 S | 2/2010 | Way et al. |
| D611,146 S | 3/2010 | Way et al. |
| 7,674,272 B2 | 3/2010 | Torrance et al. |
| 7,695,485 B2 | 4/2010 | Whitman et al. |
| 7,695,512 B2 | 4/2010 | Lashinski et al. |
| 7,697,996 B2 | 4/2010 | Manning et al. |
| 7,713,231 B2 | 5/2010 | Wulfman et al. |
| 7,713,235 B2 | 5/2010 | Torrance et al. |
| 7,713,281 B2 | 5/2010 | Leeflang et al. |
| 7,722,549 B2 | 5/2010 | Nakao |
| 7,740,626 B2 | 6/2010 | Takayama et al. |
| 7,743,960 B2 | 6/2010 | Whitman et al. |
| D619,252 S | 7/2010 | Way et al. |
| D619,253 S | 7/2010 | Way et al. |
| 7,758,594 B2 | 7/2010 | Lamson et al. |
| 7,758,613 B2 | 7/2010 | Whitman |
| D621,939 S | 8/2010 | Way et al. |
| 7,766,923 B2 | 8/2010 | Catanese et al. |
| 7,780,650 B2 | 8/2010 | Frassica et al. |
| 7,780,682 B2 | 8/2010 | Catanese et al. |
| 7,780,694 B2 | 8/2010 | Palmer et al. |
| 7,794,411 B2 | 9/2010 | Ritchart et al. |
| 7,798,813 B1 | 9/2010 | Harrel |
| 7,803,151 B2 | 9/2010 | Whitman |
| 7,806,835 B2 | 10/2010 | Hibner et al. |
| 7,811,281 B1 | 10/2010 | Rentrop |
| 7,815,655 B2 | 10/2010 | Catanese et al. |
| 7,842,009 B2 | 11/2010 | Torrance et al. |
| 7,845,538 B2 | 12/2010 | Whitman |
| 7,858,038 B2 | 12/2010 | Andreyko et al. |
| 7,875,018 B2 | 1/2011 | Tockman et al. |
| 7,875,049 B2 | 1/2011 | Eversull et al. |
| 7,890,186 B2 | 2/2011 | Wardle et al. |
| 7,890,192 B1 | 2/2011 | Kelsch et al. |
| 7,896,879 B2 | 3/2011 | Solsberg et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,464 B2 | 3/2011 | Burdorff et al. |
| 7,914,542 B2 | 3/2011 | Lamson et al. |
| D635,671 S | 4/2011 | Way et al. |
| 7,918,230 B2 | 4/2011 | Whitman et al. |

(56) References Cited

U.S. PATENT DOCUMENTS

| | | |
|---|---|---|
| 7,918,803 B2 | 4/2011 | Ritchart et al. |
| 7,930,040 B1 | 4/2011 | Kelsch et al. |
| 7,935,146 B2 | 5/2011 | Langberg et al. |
| 7,938,786 B2 | 5/2011 | Ritchie et al. |
| 7,942,830 B2 | 5/2011 | Solsberg et al. |
| 7,951,071 B2 | 5/2011 | Whitman et al. |
| 7,951,158 B2 | 5/2011 | Catanese et al. |
| 7,963,040 B2 | 6/2011 | Shan et al. |
| 7,963,433 B2 | 6/2011 | Whitman et al. |
| 7,974,710 B2 | 7/2011 | Seifert |
| 7,981,049 B2 | 7/2011 | Ritchie et al. |
| 7,981,050 B2 | 7/2011 | Ritchart et al. |
| 7,981,128 B2 | 7/2011 | To et al. |
| 7,988,726 B2 | 8/2011 | Langberg et al. |
| 7,991,258 B2 | 8/2011 | Temelkuran et al. |
| 7,992,758 B2 | 8/2011 | Whitman et al. |
| 7,993,350 B2 | 8/2011 | Ventura et al. |
| 7,993,351 B2 | 8/2011 | Worley et al. |
| 7,993,359 B1 | 8/2011 | Atwell et al. |
| 8,007,469 B2 | 8/2011 | Duffy |
| 8,007,488 B2 | 8/2011 | Ravenscroft |
| 8,007,503 B2 | 8/2011 | Catanese et al. |
| 8,007,506 B2 | 8/2011 | To et al. |
| 8,016,748 B2 | 9/2011 | Mourlas et al. |
| 8,016,844 B2 | 9/2011 | Privitera et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,025,199 B2 | 9/2011 | Whitman et al. |
| 8,043,309 B2 | 10/2011 | Catanese et al. |
| RE42,959 E | 11/2011 | Saadat et al. |
| 8,052,616 B2 | 11/2011 | Andrisek et al. |
| 8,052,659 B2 | 11/2011 | Ravenscroft et al. |
| 8,056,786 B2 | 11/2011 | Whitman et al. |
| 8,056,791 B2 | 11/2011 | Whitman |
| 8,070,762 B2 | 12/2011 | Escudero et al. |
| 8,090,430 B2 | 1/2012 | Makower et al. |
| 8,097,012 B2 | 1/2012 | Kagarise |
| 8,100,920 B2 | 1/2012 | Gambale et al. |
| 8,118,208 B2 | 2/2012 | Whitman |
| 8,126,570 B2 | 2/2012 | Manning et al. |
| 8,128,577 B2 | 3/2012 | Viola |
| 8,128,636 B2 | 3/2012 | Lui et al. |
| 8,133,214 B2 | 3/2012 | Hayase et al. |
| 8,137,377 B2 | 3/2012 | Palmer et al. |
| 8,142,442 B2 | 3/2012 | Palmer et al. |
| 8,142,446 B2 | 3/2012 | Shan |
| RE43,300 E | 4/2012 | Saadat et al. |
| 8,157,815 B2 | 4/2012 | Catanese et al. |
| 8,186,559 B1 | 5/2012 | Whitman |
| 8,187,204 B2 | 5/2012 | Miller et al. |
| 8,192,430 B2 | 6/2012 | Goode et al. |
| 8,202,229 B2 | 6/2012 | Miller et al. |
| 8,206,409 B2 | 6/2012 | Privitera et al. |
| 8,211,118 B2 | 7/2012 | Catanese et al. |
| 8,216,254 B2 | 7/2012 | McLean et al. |
| 8,235,916 B2 | 8/2012 | Whiting et al. |
| 8,236,016 B2 | 8/2012 | To et al. |
| 8,239,039 B2 | 8/2012 | Zarembo et al. |
| 8,241,272 B2 | 8/2012 | Arnold et al. |
| 8,251,916 B2 | 8/2012 | Speeg et al. |
| 8,252,015 B2 | 8/2012 | Leeflang et al. |
| 8,257,312 B2 | 9/2012 | Duffy |
| 8,272,554 B2 | 9/2012 | Whitman et al. |
| 8,273,078 B2 | 9/2012 | Muenker |
| 8,295,947 B2 | 10/2012 | Lamson et al. |
| 8,303,511 B2 | 11/2012 | Eigler et al. |
| 8,323,240 B2 | 12/2012 | Wulfman et al. |
| 8,326,437 B2 | 12/2012 | Cully et al. |
| 8,333,740 B2 | 12/2012 | Shippert |
| 8,333,776 B2 | 12/2012 | Cheng et al. |
| 8,337,516 B2 | 12/2012 | Escudero et al. |
| 8,343,167 B2 | 1/2013 | Henson |
| 8,343,187 B2 | 1/2013 | Lamson et al. |
| 8,353,899 B1 | 1/2013 | Wells et al. |
| 8,361,094 B2 | 1/2013 | To et al. |
| 8,361,097 B2 | 1/2013 | Patel et al. |
| 8,364,280 B2 | 1/2013 | Marnfeldt et al. |
| 8,372,098 B2 | 2/2013 | Tran |
| 8,394,110 B2 | 3/2013 | Catanese et al. |
| 8,394,113 B2 | 3/2013 | Wei et al. |
| 8,425,535 B2 | 4/2013 | McLean et al. |
| 9,028,520 B2 | 5/2015 | Taylor et al. |
| 9,345,508 B2 | 5/2016 | Hendrick |
| 9,801,650 B2 | 10/2017 | Taylor et al. |
| 2001/0005789 A1 | 6/2001 | Root et al. |
| 2001/0016717 A1 | 8/2001 | Haarala et al. |
| 2001/0025174 A1 | 9/2001 | Daniel et al. |
| 2001/0031981 A1 | 10/2001 | Evans et al. |
| 2001/0039427 A1 | 11/2001 | Dinger et al. |
| 2001/0041899 A1 | 11/2001 | Foster |
| 2001/0044568 A1 | 11/2001 | Langberg et al. |
| 2002/0002372 A1 | 1/2002 | Jahns et al. |
| 2002/0007204 A1 | 1/2002 | Goode |
| 2002/0010475 A1 | 1/2002 | Lui |
| 2002/0010487 A1 | 1/2002 | Evans et al. |
| 2002/0016628 A1 | 2/2002 | Langberg et al. |
| 2002/0045811 A1 | 4/2002 | Kittrell et al. |
| 2002/0065543 A1 | 5/2002 | Gomperz et al. |
| 2002/0068954 A1 | 6/2002 | Foster |
| 2002/0087151 A1 | 7/2002 | Mody et al. |
| 2002/0103477 A1 | 8/2002 | Grasso et al. |
| 2002/0103532 A1 | 8/2002 | Langberg et al. |
| 2002/0103533 A1 | 8/2002 | Langberg et al. |
| 2002/0123785 A1 | 9/2002 | Zhang et al. |
| 2002/0151961 A1 | 10/2002 | Lashinski et al. |
| 2002/0183735 A1 | 12/2002 | Edwards et al. |
| 2002/0188278 A1 | 12/2002 | Tockman et al. |
| 2003/0009146 A1 | 1/2003 | Muni et al. |
| 2003/0036788 A1 | 2/2003 | Coe et al. |
| 2003/0050630 A1 | 3/2003 | Mody et al. |
| 2003/0050631 A1 | 3/2003 | Mody et al. |
| 2003/0055444 A1 | 3/2003 | Evans et al. |
| 2003/0055445 A1 | 3/2003 | Evans et al. |
| 2003/0069575 A1 | 4/2003 | Chin et al. |
| 2003/0073985 A1 | 4/2003 | Mueller et al. |
| 2003/0078562 A1 | 4/2003 | Makower et al. |
| 2003/0105451 A1 | 6/2003 | Westlund et al. |
| 2003/0125619 A1 | 7/2003 | Manning et al. |
| 2003/0167056 A1 | 9/2003 | Jahns et al. |
| 2003/0187460 A1 | 10/2003 | Chin et al. |
| 2003/0187461 A1 | 10/2003 | Chin |
| 2003/0199921 A1 | 10/2003 | Palmer et al. |
| 2003/0204202 A1 | 10/2003 | Palmer et al. |
| 2003/0208209 A1 | 11/2003 | Gambale et al. |
| 2003/0229323 A1 | 12/2003 | Haarala et al. |
| 2003/0229353 A1 | 12/2003 | Cragg |
| 2004/0006358 A1 | 1/2004 | Wulfman et al. |
| 2004/0010248 A1 | 1/2004 | Appling et al. |
| 2004/0015193 A1 | 1/2004 | Lamson et al. |
| 2004/0019359 A1 | 1/2004 | Worley et al. |
| 2004/0049208 A1 | 3/2004 | Hill et al. |
| 2004/0054368 A1 | 3/2004 | Truckai et al. |
| 2004/0054388 A1 | 3/2004 | Osypka |
| 2004/0059348 A1 | 3/2004 | Geske et al. |
| 2004/0064024 A1 | 4/2004 | Sommer |
| 2004/0068256 A1 | 4/2004 | Rizoiu et al. |
| 2004/0068288 A1 | 4/2004 | Palmer et al. |
| 2004/0093016 A1 | 5/2004 | Root et al. |
| 2004/0097788 A1 | 5/2004 | Mourlas et al. |
| 2004/0102804 A1 | 5/2004 | Chin |
| 2004/0102841 A1 | 5/2004 | Langberg et al. |
| 2004/0111101 A1 | 6/2004 | Chin |
| 2004/0116939 A1 | 6/2004 | Goode |
| 2004/0116992 A1 | 6/2004 | Wardle et al. |
| 2004/0133220 A1 | 7/2004 | Lashinski et al. |
| 2004/0138562 A1 | 7/2004 | Makower et al. |
| 2004/0138744 A1 | 7/2004 | Lashinski et al. |
| 2004/0143284 A1 | 7/2004 | Chin |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0153096 A1 | 8/2004 | Goode et al. |
| 2004/0153098 A1 | 8/2004 | Chin et al. |

(56) References Cited

U.S. PATENT DOCUMENTS

| | | |
|---|---|---|
| 2004/0153146 A1 | 8/2004 | Lashinski et al. |
| 2004/0172116 A1 | 9/2004 | Seifert et al. |
| 2004/0176840 A1 | 9/2004 | Langberg et al. |
| 2004/0181249 A1 | 9/2004 | Torrance et al. |
| 2004/0199191 A1 | 10/2004 | Schwartz |
| 2004/0216748 A1 | 11/2004 | Chin |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0236397 A1 | 11/2004 | Coe et al. |
| 2004/0243123 A1 | 12/2004 | Grasso et al. |
| 2004/0243162 A1 | 12/2004 | Wulfman et al. |
| 2004/0254534 A1 | 12/2004 | Bjorkman et al. |
| 2004/0260322 A1 | 12/2004 | Rudko et al. |
| 2004/0267276 A1 | 12/2004 | Camino et al. |
| 2004/0267304 A1 | 12/2004 | Zannis et al. |
| 2005/0004644 A1 | 1/2005 | Kelsch et al. |
| 2005/0025798 A1 | 2/2005 | Moulis |
| 2005/0027337 A1 | 2/2005 | Rudko et al. |
| 2005/0038419 A9 | 2/2005 | Arnold et al. |
| 2005/0060030 A1 | 3/2005 | Lashinski et al. |
| 2005/0065561 A1 | 3/2005 | Manning et al. |
| 2005/0090748 A1 | 4/2005 | Makower et al. |
| 2005/0096740 A1 | 5/2005 | Langberg et al. |
| 2005/0131399 A1 | 6/2005 | Loeb et al. |
| 2005/0149104 A1 | 7/2005 | Leeflang et al. |
| 2005/0149105 A1 | 7/2005 | Leeflang et al. |
| 2005/0197623 A1 | 9/2005 | Leeflang et al. |
| 2005/0222607 A1 | 10/2005 | Palmer et al. |
| 2005/0228402 A1 | 10/2005 | Hofmann |
| 2005/0228452 A1 | 10/2005 | Mourlas et al. |
| 2005/0251116 A1 | 11/2005 | Steinke et al. |
| 2005/0259942 A1 | 11/2005 | Temelkuran et al. |
| 2005/0267557 A1 | 12/2005 | Flynn et al. |
| 2005/0273090 A1 | 12/2005 | Nieman et al. |
| 2005/0283143 A1 | 12/2005 | Rizoiu |
| 2005/0288596 A1 | 12/2005 | Eigler et al. |
| 2005/0288604 A1 | 12/2005 | Eigler et al. |
| 2005/0288654 A1 | 12/2005 | Nieman et al. |
| 2005/0288722 A1 | 12/2005 | Eigler et al. |
| 2006/0041250 A1 | 2/2006 | Poleo |
| 2006/0052660 A1 | 3/2006 | Chin |
| 2006/0084839 A1 | 4/2006 | Mourlas et al. |
| 2006/0100663 A1 | 5/2006 | Palmer et al. |
| 2006/0116746 A1 | 6/2006 | Chin |
| 2006/0116757 A1 | 6/2006 | Lashinski et al. |
| 2006/0167417 A1 | 7/2006 | Kratz et al. |
| 2006/0173440 A1 | 8/2006 | Lamson et al. |
| 2006/0217755 A1 | 9/2006 | Eversull et al. |
| 2006/0229490 A1 | 10/2006 | Chin |
| 2006/0235431 A1 | 10/2006 | Goode et al. |
| 2006/0247751 A1 | 11/2006 | Seifert |
| 2006/0253179 A1 | 11/2006 | Goode et al. |
| 2006/0265042 A1 | 11/2006 | Catanese et al. |
| 2006/0276871 A1 | 12/2006 | Lamson et al. |
| 2006/0287574 A1 | 12/2006 | Chin |
| 2007/0005084 A1 | 1/2007 | Clague et al. |
| 2007/0015964 A1 | 1/2007 | Eversull et al. |
| 2007/0016130 A1 | 1/2007 | Leeflang et al. |
| 2007/0021812 A1 | 1/2007 | Manning et al. |
| 2007/0049929 A1 | 3/2007 | Catanese et al. |
| 2007/0050003 A1 | 3/2007 | Zarembo et al. |
| 2007/0083217 A1 | 4/2007 | Eversull et al. |
| 2007/0100410 A1 | 5/2007 | Lamson et al. |
| 2007/0106328 A1 | 5/2007 | Wardle et al. |
| 2007/0129710 A1 | 6/2007 | Rudko et al. |
| 2007/0142846 A1 | 6/2007 | Catanese et al. |
| 2007/0197861 A1 | 8/2007 | Reiley et al. |
| 2007/0198020 A1 | 8/2007 | Reiley et al. |
| 2007/0232981 A1 | 10/2007 | Ravenscroft et al. |
| 2007/0265648 A1 | 11/2007 | Cohen |
| 2007/0276412 A1 | 11/2007 | Catanese et al. |
| 2007/0293853 A1 | 12/2007 | Truckai et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0015625 A1 | 1/2008 | Ventura et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039889 A1 | 2/2008 | Lamson et al. |
| 2008/0039893 A1 | 2/2008 | McLean et al. |
| 2008/0039894 A1 | 2/2008 | Catanese et al. |
| 2008/0045986 A1 | 2/2008 | To et al. |
| 2008/0051756 A1 | 2/2008 | Makower et al. |
| 2008/0058759 A1 | 3/2008 | Makower et al. |
| 2008/0071341 A1 | 3/2008 | Goode et al. |
| 2008/0071342 A1 | 3/2008 | Goode et al. |
| 2008/0097426 A1 | 4/2008 | Root et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0125748 A1 | 5/2008 | Patel |
| 2008/0147061 A1 | 6/2008 | Goode et al. |
| 2008/0154293 A1 | 6/2008 | Taylor |
| 2008/0183163 A1 | 7/2008 | Lampropoulos et al. |
| 2008/0208105 A1 | 8/2008 | Zelickson et al. |
| 2008/0221560 A1 | 9/2008 | Arai et al. |
| 2008/0228208 A1 | 9/2008 | Wulfman et al. |
| 2008/0249516 A1 | 10/2008 | Muenker |
| 2008/0262516 A1 | 10/2008 | Gambale et al. |
| 2008/0275497 A1 | 11/2008 | Palmer et al. |
| 2008/0275498 A1 | 11/2008 | Palmer et al. |
| 2008/0281308 A1 | 11/2008 | Neuberger et al. |
| 2008/0287888 A1 | 11/2008 | Ravenscroft |
| 2008/0306333 A1 | 12/2008 | Chin |
| 2009/0012510 A1 | 1/2009 | Bertolero et al. |
| 2009/0018523 A1 | 1/2009 | Lamson et al. |
| 2009/0018553 A1 | 1/2009 | McLean et al. |
| 2009/0018565 A1 | 1/2009 | To et al. |
| 2009/0034927 A1 | 2/2009 | Temelkuran et al. |
| 2009/0036871 A1 | 2/2009 | Hayase et al. |
| 2009/0054918 A1 | 2/2009 | Henson |
| 2009/0060977 A1 | 3/2009 | Lamson et al. |
| 2009/0071012 A1 | 3/2009 | Shan et al. |
| 2009/0076522 A1 | 3/2009 | Shan |
| 2009/0131907 A1 | 5/2009 | Chin et al. |
| 2009/0157045 A1 | 6/2009 | Haarala et al. |
| 2009/0192439 A1 | 7/2009 | Lamson et al. |
| 2009/0204128 A1 | 8/2009 | Lamson et al. |
| 2009/0221994 A1 | 9/2009 | Neuberger et al. |
| 2009/0222025 A1 | 9/2009 | Catanese et al. |
| 2009/0227999 A1 | 9/2009 | Willis et al. |
| 2009/0234378 A1 | 9/2009 | Escudero et al. |
| 2010/0004606 A1 | 1/2010 | Hansen et al. |
| 2010/0016836 A1 | 1/2010 | Makower et al. |
| 2010/0030154 A1 | 2/2010 | Duffy |
| 2010/0030161 A1 | 2/2010 | Duffy |
| 2010/0030247 A1 | 2/2010 | Pikus et al. |
| 2010/0030262 A1 | 2/2010 | McLean et al. |
| 2010/0030263 A1 | 2/2010 | Cheng et al. |
| 2010/0049225 A1 | 2/2010 | To et al. |
| 2010/0063488 A1 | 3/2010 | Fischer et al. |
| 2010/0125253 A1 | 5/2010 | Olson et al. |
| 2010/0137873 A1 | 6/2010 | Grady et al. |
| 2010/0160952 A1 | 6/2010 | Leeflang et al. |
| 2010/0191165 A1 | 7/2010 | Appling et al. |
| 2010/0198194 A1 | 8/2010 | Manning et al. |
| 2010/0198229 A1 | 8/2010 | Olomutzki et al. |
| 2010/0217277 A1 | 8/2010 | Truong |
| 2010/0222737 A1 | 9/2010 | Arnold et al. |
| 2010/0222787 A1 | 9/2010 | Goode et al. |

(56) References Cited

U.S. PATENT DOCUMENTS

| | | |
|---|---|---|
| 2010/0240951 A1 | 9/2010 | Catanese et al. |
| 2010/0256616 A1 | 10/2010 | Katoh et al. |
| 2010/0280496 A1 | 11/2010 | Shippert |
| 2010/0324472 A1 | 12/2010 | Wulfman |
| 2010/0331793 A1 | 12/2010 | Tulleken |
| 2011/0004238 A1 | 1/2011 | Palmer et al. |
| 2011/0009957 A1 | 1/2011 | Langberg et al. |
| 2011/0022057 A1 | 1/2011 | Eigler et al. |
| 2011/0028959 A1 | 2/2011 | Chasan |
| 2011/0034790 A1 | 2/2011 | Mourlas et al. |
| 2011/0040238 A1 | 2/2011 | Wulfman et al. |
| 2011/0040312 A1 | 2/2011 | Lamson et al. |
| 2011/0040315 A1 | 2/2011 | To et al. |
| 2011/0040326 A1 | 2/2011 | Wei et al. |
| 2011/0046648 A1 | 2/2011 | Johnston et al. |
| 2011/0054493 A1 | 3/2011 | McLean et al. |
| 2011/0060349 A1 | 3/2011 | Cheng et al. |
| 2011/0071440 A1 | 3/2011 | Torrance et al. |
| 2011/0105947 A1 | 5/2011 | Fritscher-Ravens et al. |
| 2011/0106004 A1 | 5/2011 | Eubanks et al. |
| 2011/0106099 A1 | 5/2011 | Duffy et al. |
| 2011/0112548 A1 | 5/2011 | Fifer et al. |
| 2011/0112562 A1 | 5/2011 | Torrance |
| 2011/0112563 A1 | 5/2011 | To et al. |
| 2011/0112564 A1 | 5/2011 | Wolf |
| 2011/0118660 A1 | 5/2011 | Torrance et al. |
| 2011/0144423 A1 | 6/2011 | Tong et al. |
| 2011/0144425 A1 | 6/2011 | Catanese et al. |
| 2011/0151463 A1 | 6/2011 | Wulfman |
| 2011/0152607 A1 | 6/2011 | Catanese et al. |
| 2011/0152906 A1 | 6/2011 | Escudero et al. |
| 2011/0152907 A1 | 6/2011 | Escudero et al. |
| 2011/0160747 A1 | 6/2011 | McLean et al. |
| 2011/0160748 A1 | 6/2011 | Catanese et al. |
| 2011/0166564 A1 | 7/2011 | Merrick et al. |
| 2011/0178543 A1 | 7/2011 | Chin et al. |
| 2011/0190758 A1 | 8/2011 | Lamson et al. |
| 2011/0196298 A1 | 8/2011 | Anderson et al. |
| 2011/0196355 A1 | 8/2011 | Mitchell et al. |
| 2011/0208207 A1 | 8/2011 | Bowe et al. |
| 2011/0213398 A1 | 9/2011 | Chin et al. |
| 2011/0218528 A1 | 9/2011 | Ogata et al. |
| 2011/0238078 A1 | 9/2011 | Goode et al. |
| 2011/0238102 A1 | 9/2011 | Gutfinger et al. |
| 2011/0245751 A1 | 10/2011 | Hofmann |
| 2011/0251629 A1 | 10/2011 | Galdonik et al. |
| 2011/0257592 A1 | 10/2011 | Ventura et al. |
| 2011/0270169 A1 | 11/2011 | Gardeski et al. |
| 2011/0270170 A1 | 11/2011 | Gardeski et al. |
| 2011/0270289 A1 | 11/2011 | To et al. |
| 2011/0300010 A1 | 12/2011 | Jarnagin et al. |
| 2011/0301417 A1 | 12/2011 | Mourlas et al. |
| 2011/0301626 A1 | 12/2011 | To et al. |
| 2012/0035590 A1 | 2/2012 | Whiting et al. |
| 2012/0041422 A1 | 2/2012 | Whiting et al. |
| 2012/0053564 A1 | 3/2012 | Ravenscroft |
| 2012/0065659 A1 | 3/2012 | To |
| 2012/0083810 A1 | 4/2012 | Escudero et al. |
| 2012/0083826 A1 | 4/2012 | Chao et al. |
| 2012/0095447 A1 | 4/2012 | Fojtik |
| 2012/0095479 A1 | 4/2012 | Bowe et al. |
| 2012/0097174 A1 | 4/2012 | Spotnitz et al. |
| 2012/0123411 A1 | 5/2012 | Ibrahim et al. |
| 2012/0136341 A1 | 5/2012 | Appling et al. |
| 2012/0165827 A1 | 6/2012 | Khairkhahan et al. |
| 2012/0165861 A1 | 6/2012 | Palmer et al. |
| 2012/0191015 A1 | 7/2012 | Zannis et al. |
| 2012/0209173 A1 | 8/2012 | Hayase et al. |
| 2012/0215305 A1 | 8/2012 | Le et al. |
| 2012/0239008 A1 | 9/2012 | Fojtik |
| 2012/0245600 A1 | 9/2012 | McLean et al. |
| 2012/0253229 A1 | 10/2012 | Cage |
| 2012/0265183 A1 | 10/2012 | Tulleken et al. |
| 2012/0323252 A1 | 12/2012 | Booker |
| 2012/0323253 A1 | 12/2012 | Garai et al. |
| 2012/0330292 A1 | 12/2012 | Shadduck et al. |
| 2013/0006228 A1 | 1/2013 | Johnson et al. |
| 2013/0035676 A1 | 2/2013 | Mitchell et al. |
| 2013/0096582 A1 | 4/2013 | Cheng et al. |
| 2013/0103047 A1 | 4/2013 | Steingisser et al. |
| 2014/0031800 A1 | 1/2014 | Ben Oren et al. |
| 2015/0216547 A1 | 8/2015 | Hendrick |
| 2016/0317173 A1 | 11/2016 | Hendrick |

FOREIGN PATENT DOCUMENTS

| | | |
|---|---|---|
| WO | 1991017711 A1 | 11/1991 |
| WO | 1995033513 A1 | 12/1995 |
| WO | 1999007295 A1 | 2/1999 |
| WO | 1999049937 A1 | 10/1999 |
| WO | 1999058066 A1 | 11/1999 |
| WO | 2001076680 A1 | 10/2001 |
| WO | 2002049690 A9 | 5/2003 |
| WO | 2004080345 A2 | 9/2004 |
| WO | 2004080507 A2 | 9/2004 |
| WO | 2006007410 A2 | 1/2006 |
| WO | 2008005888 A2 | 1/2008 |
| WO | 2008005891 A2 | 1/2008 |
| WO | 2008042987 A2 | 4/2008 |
| WO | 2009005779 A1 | 1/2009 |
| WO | 2009054968 A1 | 4/2009 |
| WO | 2009065082 A1 | 5/2009 |
| WO | 2009126309 A2 | 10/2009 |
| WO | 2011003113 A1 | 1/2011 |
| WO | 2011084863 A2 | 7/2011 |
| WO | 2011133941 A2 | 10/2011 |
| WO | 2011162595 A1 | 12/2011 |
| WO | 2012009697 A4 | 4/2012 |
| WO | 2012098335 A1 | 7/2012 |
| WO | 2012114333 A1 | 8/2012 |
| WO | 2012177117 A1 | 12/2012 |
| WO | 2013036588 A1 | 3/2013 |

OTHER PUBLICATIONS

U.S. Appl. No. 62/058,790 entitled Medical Device for Removing an Implanted Object filed Oct. 2, 2014.

U.S. Appl. No. 62/094,808 entitled Multiple Configuration Surgical Cutting Device filed Dec. 19, 2014.

U.S. Appl. No. 62/113,865 entitled Medical Device for Removing an Implanted Object filed Feb. 9, 2015.

Decision to Grant for European Patent Application No. 07255018.9, dated Aug. 8, 2013, 2 pages.

Department of Health and Ageing in Australian Government, "Horizon Scanning Technology Prioritising: Laser Extraction Systems." 2010. 15 pages.

EP extended Search Report dated Oct. 21, 2009; Application No. 07255019.7, 8 pages.

Extended European Search Report for European Application No. 07255018.9, dated Nov. 12, 2010, 7 pages.

Final Action for U.S. Appl. No. 11/615,005, dated Nov. 9, 2009, 10 pages.

Final Action for U.S. Appl. No. 11/615,005, dated Nov. 21, 2013, 20 pages.

Final Action for U.S. Appl. No. 11/615,006 dated Oct. 26, 2009, 9 pages.

Intent to Grant for European Patent Application No. 07255018.9, dated Nov. 29, 2012, 7 pages.

International Search Report and Written Opinion for International Patent Application No. PCT/US2013/059434, dated Dec. 13, 2013, 14 pages.

International Search Report and Written Opinion issued in PCT/US2014/019258, dated Aug. 8, 2014, 21 pages.

International Search Report and Written Opinion issued in PCT/US2014/021167 dated Jun. 26, 2014, 19 pages.

International Search Report and Written Opinion issued in PCT/US2014/026496 dated Jul. 30, 2014, 16 pages.

International Search Report and Written Opinion issued in PCT/US2015/016899, dated May 1, 2015, 14 pages.

(56) References Cited

OTHER PUBLICATIONS

Notice of Allowance for European Patent Application No. 07255018.9, dated Jul. 26, 2012, 47 pages.
Notice of Allowance for Japan Patent Application No. 2007-333273, dated Jan. 16, 2014, 3 pages.
Official Action for European Patent Application No. 07255018.9, dated Jul. 19, 2011, 3 pages.
Official Action for U.S. Appl. No. 11/615,005, dated Apr. 16, 2009, 13 pages.
Official Action for U.S. Appl. No. 11/615,005, dated Feb. 11, 2011, 12 pages.
Official Action for U.S. Appl. No. 11/615,005, dated Jul. 21, 2010, 10 pages.
Official Action for U.S. Appl. No. 11/615,005, dated Mar. 14, 2013, 16 pages.
Official Action for U.S. Appl. No. 13/800,728, dated Jan. 16, 2014, 14 pages.
Official Action for U.S. Appl. No. 11/615,006 dated Apr. 24, 2009, 7 pages.
Official Action for U.S. Appl. No. 11/615,006 dated Feb. 17, 2010, 8 pages.
Official Action for U.S. Appl. No. 11/615,006 dated Jul. 20, 2010, 9 pages.
Official Action for U.S. Appl. No. 11/615,006 dated Mar. 14, 2013, 16 pages.
Official Action for U.S. Appl. No. 11/615,006 dated Nov. 22, 2013, 16 pages.
Official Action with English translation for Japan Patent Application No. 2007-333173, dated Apr. 30, 2013, 5 pages.
Official Action with English translation for Japan Patent Application No. 2007-333173, dated Aug. 13, 2012, 7 pages.
Official Action with English translation for Japan Patent Application No. 2007-333273, dated Jul. 30, 2012, 7 pages.
Official Action with English translation for Japan Patent Application No. 2007-333273, dated Jun. 6, 2013, 10 pages.
PCT Application No. PCT/US2015/016899 entitled Medical Device for Removing an Implanted Object filed Feb. 20, 2015.
PCT Application No. PCT/US2015/018305 entitled Multiple Configuration Surgical Cutting Device filed Mar. 2, 2015.
U.S. Appl. No. 13/800,651 entitled System and Method of Ablative Cutting and Pulsed Vacuum Aspiration, filed Mar. 13, 2013.
U.S. Appl. No. 13/800,675 entitled Laser Catheter With Helical Internal Lumen, filed Mar. 13, 2013.
U.S. Appl. No. 13/800,700 entitled Device and Method of Ablative Cutting With Helical Tip, filed Mar. 13, 2013.
U.S. Appl. No. 13/800,728 entitled Laser Ablation Catheter, filed Mar. 13, 2013.
U.S. Appl. No. 13/828,231 entitled Tissue Slitting Methods and Systems, filed Mar. 14, 2013.
U.S. Appl. No. 13/828,310 entitled Tissue Slitting Methods and Systems, filed Mar. 14, 2013.
U.S. Appl. No. 13/828,383 entitled Tissue Slitting Methods and Systems, filed Mar. 14, 2013.
U.S. Appl. No. 13/828,441 entitled Tissue Slitting Methods and Systems, filed Mar. 14, 2013.
U.S. Appl. No. 13/828,536 entitled Expandable Lead Jacket, filed Mar. 14, 2013.
U.S. Appl. No. 13/828,638 entitled Lead Removal Sleeve, filed Mar. 14, 2013.
U.S. Appl. No. 13/834,405 entitled Retractable Blade for Lead Removal Device, filed Mar. 15, 2013.
U.S. Appl. No. 14/577,976 entitled Surgical Instrument Including an Inwardly Deflecting Cutting Tip for Removing an Implanted Object filed Dec. 19, 2014.
U.S. Appl. No. 14/589,688 entitled Retractable Separating Systems and Methods filed Jan. 5, 2015.
U.S. Appl. No. 14/627,851 entitled Medical Device for Removing an Implanted Object filed Feb. 20, 2015.
U.S. Appl. No. 14/627,950 entitled Medical Device for Removing an Implanted Object filed Feb. 20, 2015.
U.S. Appl. No. 14/635,742 entitled Multiple Configuration Surgical Cutting Device filed Mar. 2, 2015.
U.S. Appl. No. 61/793,597 entitled Surgical Instrument for Removing an Implanted Object filed Mar. 15, 2013.
U.S. Appl. No. 61/987,993 entitled Dual Mode Mechanical Catheter Cutting System filed May 2, 2014.

* cited by examiner

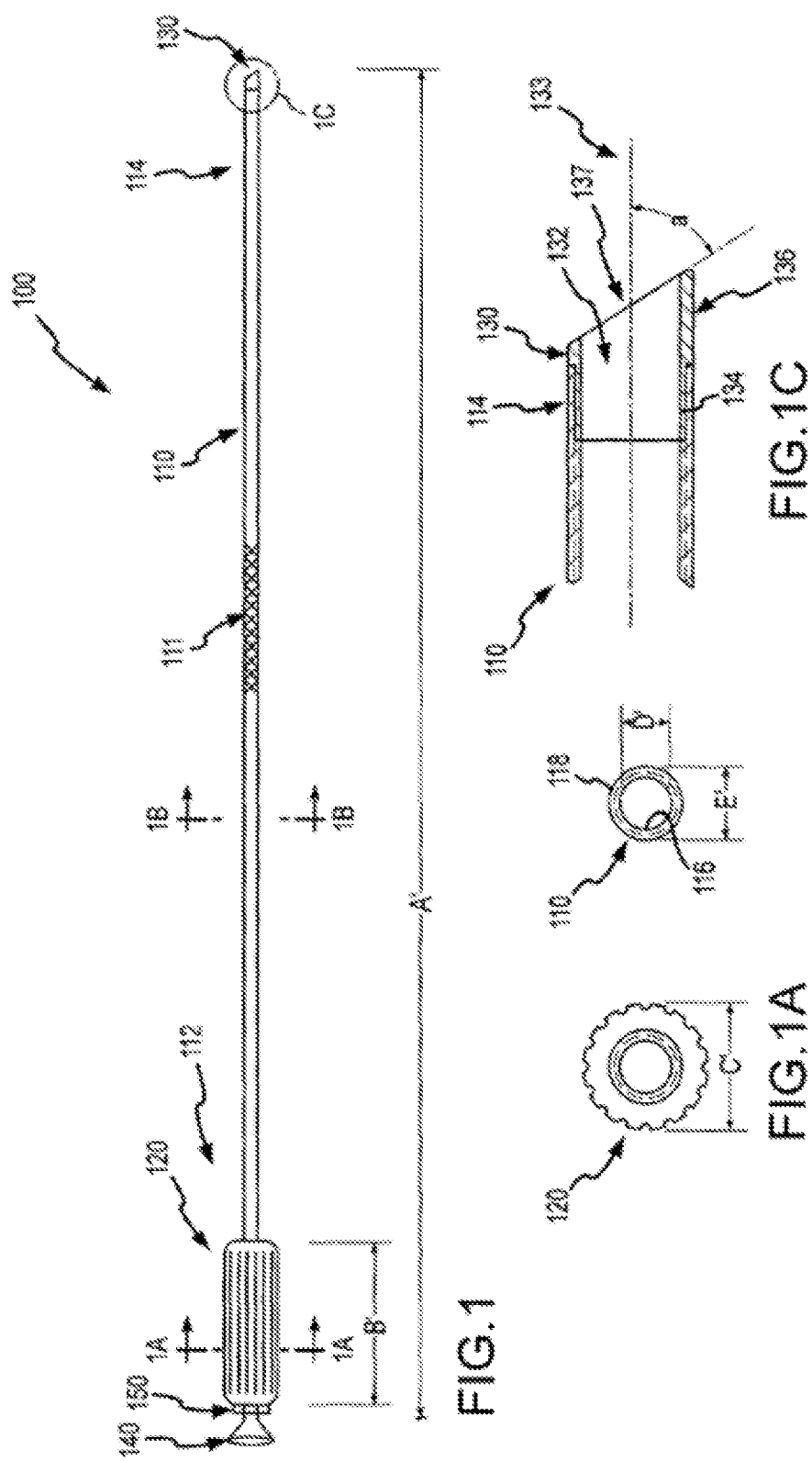

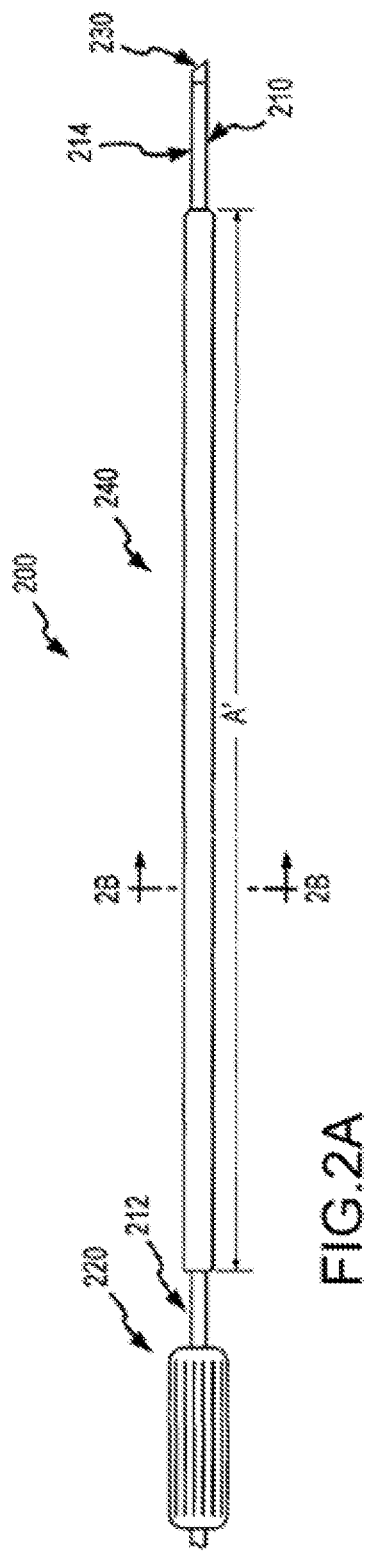
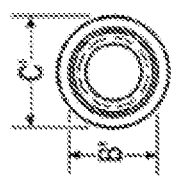
FIG.2A
FIG.2B

TISSUE SEPARATING SYSTEMS AND METHODS

CROSS-REFERENCES TO RELATED APPLICATIONS

This application is a continuation of U.S. application Ser. No. 14/682,779, filed Apr. 9, 2015, now U.S. Pat. No. 9,801,650, and titled "TISSUE SEPARATING SYSTEMS AND METHODS," which is a continuation of U.S. patent application Ser. No. 11/615,005, filed Dec. 22, 2006, now U.S. Pat. No. 9,028,520, and titled "TISSUE SEPARATING SYSTEMS AND METHODS," the entire contents of which are incorporated herein by reference for all purposes. This application is related to U.S. patent application Ser. No. 11/615,006, filed Dec. 22, 2006, now U.S. Pat. No. 8,961,551, and titled "RETRACTABLE SEPARATING SYSTEMS AND METHODS," the entire contents of which are incorporated herein by reference for all purposes.

BACKGROUND OF THE INVENTION

The present application relates generally to systems and methods for separating tissue in a patient, and more specifically, to techniques for separating pacing leads from a patient.

Cardiac pacing systems typically include a pacemaker and a pacing lead, which are placed inside the body of a patient. The pacemaker includes a power source and circuitry configured to send timed electrical pulses to the pacing lead. The pacing lead carries the electrical pulse to the heart to initiate a heartbeat, and transmits information about the heart's electrical activity to the pacemaker. The pacing lead can include a fixation mechanism that holds the lead to the cardiac tissue. In some cases, a pacing lead is inserted through a vein and guided into a heart chamber where it is attached with the heart. In other instances, a pacing lead is attached to the outside of the heart. A common problem associated with pacing leads is the development of scar tissue or adhesions where the pacing lead contacts the patient's body tissue. Patient tissue can become attached with the pacing lead, and thus removal or extraction of the pacing lead may present complications.

Current pacing lead extraction techniques include mechanical traction, mechanical devices, and laser devices. Mechanical traction is often accomplished by inserting a locking stylet into the lead and pulling to remove it. In some cases, for example where mechanical traction is ineffective, dilating telescopic sheaths can be used to strip away the scar tissue adhering the lead to the body. Unfortunately, metal sheaths that are currently used to strip scar tissue from implanted leads often cannot traverse the tortuous lead path, and in many instances can only be used in proximal locations. Currently used plastic sheaths may be able to access certain distal lead locations, but often suffer from poor torque properties, low radiopacity, and ineffective penetration into hard tissue because they have soft tips that deform when in contact with the hard tissue. Dilation techniques often involve pushing tissue away from the lead when the sheath is pushed longitudinally along the lead. However, longitudinal forces can be easily lost during the procedure by tortuousity or curvature in the lead and by friction encountered within the anatomy or over the pacing lead. Longitudinal forces also may require heavy counter traction on the lead-that can result in pacing lead breakage. Some mechanical sheaths have proposed trigger mechanisms for extending a blade from a sheath. At least some of these devices, however, involve complicated activation mechanisms and may not be well suited for negotiating the tortuous paths that exist in certain vascular or physiological environments. Laser devices typically employ laser energy to cut the scar tissue away from the lead thus allowing for removal. Although effective in some circumstances for removing chronic implanted pacing leads, many laser systems can be expensive and unaffordable to many treatment centers.

What is needed are improved mechanical devices and methods for extracting pacing leads as well as other objects. These techniques can provide effective alternatives to currently used dilating lead extraction sheaths and laser systems.

BRIEF SUMMARY OF THE INVENTION

Advantageously, embodiments of the present invention encompass separating devices having improved separating surfaces and shapes that are well suited for freeing pacing leads from adherent scar tissue. For example, a separating tip or element can provide a bevel or angle to enhance contact between a separating tip blade and the patient tissue during rotation of the tip. In some cases, a separating tip provides a separating surface that can be lightly forced against a tissue without separating the tissue, and that can separate the tissue when pressed more forcefully against the tissue or when rotated relative to the tissue. Separating systems can be configured to extract pacing leads primarily by torque. An exemplary separating system involves a torqueable and flexible polymer sheath with a durable, radiopaque tip section that includes hard plastic or metal. The shaft can be composed of a braided composite construction to provide flexibility along with a 1:1 torque response. The system may also include a handle to allow for improved rotation capabilities. When the sheath is rotated, a cutting tip can strip, dilate, or cut adhered tissue from the lead in an axial manner. The configurations provided herein allow pacing lead extraction under reduced force, thereby minimizing the incidence of lead breakage and protecting the safety of the patient. By combining such torque characteristics with distal surface cutting edges, it is possible to effectively penetrate resistant scar tissue when necessary, while maintaining a safe, non-separating profile when the sheath is advanced longitudinally over a pacing lead.

Many of the embodiments described herein refer to cutting elements, cutting assemblies, cutters, and the like, which often include items for cutting tissue, however it is understood that these cutting features can be replaced with or referred to as stripping or dilating elements, stripping or dilating assemblies, or strippers or dilators. Similarly, these cutting features may be referred to as separating elements, separating assemblies, or separators. Stripping features can include items for stripping tissue from pacing leads and other objects within the body of a patient. Relatedly, dilating features can include items for dilating tissue surrounding or near pacing leads and other objects within the body of a patient. Cutting features or procedures can be used or referred to interchangeably with stripping features or procedures, and with dilating features or procedures. Methods that include stripping or dilating tissue may or may not include cutting tissue. In some embodiments, cutting, stripping, or dilating elements or procedures, or any combinations thereof, may be referred to as separating elements or procedures. For example, a separator may refer to or encompass a cutter, a stripper, or a dilator, or any combination thereof. The separating devices, sheath configurations, and other systems and methods described herein are well suited for use with retractable lead extraction techniques disclosed in previously incorporated U.S. patent application Ser. No. 11/605,006, filed Dec. 22, 2006 (Retractable Separating Systems and Methods). Such separating and retractable extraction devices can be used in conjunction with lead locking devices in an explant procedure. In an exemplary method, a lead is disconnected from a pacemaker, and a lead locking device is inserted into or coupled with the lead. A separating or retractable extraction system can be placed over the lead and the lead locking device, and advanced distally so as to separate tissue that is attached with or surrounding the lead. Lead locking devices are often useful in providing traction with a pacing or defibrillator lead without breaking or damaging the lead.

In a first aspect, embodiments of the present invention provide a system for separating an object from a patient tissue. The system can include a sheath having a proximal end and a distal end. The system can also include a cylindrical separator coupled with the distal end of the sheath. The separator can have an internal lumen, a proximal end, and a distal end having a separating mechanism. The separating mechanism can include an abrasive material. In some cases, the abrasive material includes diamond, aluminum carbide, silica carbide, or the like. The distal end of the separator can define a plane, and the internal lumen of the separator can define a central longitudinal axis. An acute angle between the plane and the central longitudinal axis can be within a range from about 10 degrees to about 65 degrees or from about 30 degrees to about 85 degrees. The separator may include a cutting member, a dilating member, a stripping member, or the like.

In another aspect, embodiments of the present invention provide a system for separating an object from a patient tissue, where the system includes an internal sheath having a proximal end and a distal end, an external sheath having a proximal end and a distal end, an internal separator coupled with the distal end of the internal sheath, the internal separator having a first separating mechanism, and an external separator coupled with the distal end of the external sheath, the external separator having a second separating mechanism. The internal separator can be disposed at least partially within the external separator, and the internal and external separators can be configured for relative rotational movement that brings the first separating mechanism and the second separating mechanism together. In some cases, the internal separator includes an internal cutting member, an internal stripping member, an internal dilating member, or the like, and the external separator includes an external cutting member, an external stripping member, an external dilating member, or the like. In some aspects, the first separating mechanism includes a first cutting blade, a first stripping blade, a first dilating blade, or the like, and the second separating mechanism includes a second cutting blade, a second stripping blade, a second dilating blade, or the like. In another aspect, embodiments provide a separating system that includes a sheath having a distal end, and a cylindrical separator. The separator can include a distal end having a separating mechanism, and a proximal end coupled with the sheath distal end. The distal end of the cylindrical separator can define a plane that is substantially perpendicular to a central longitudinal axis of the cylindrical separator. In some cases, the sheath includes a proximal end that is less flexible than the distal end of the sheath. The distal end of the sheath can have bending stiffness less than about 6 lb/in. The sheath can have a torsional transmission of greater than about 0.177 pound-inch. In some embodiments, the sheath includes a braid. The separator can include a cutting member, a stripping member, a dilating member, or the like. The separating mechanism can include a cutting blade, a stripping blade, a dilating blade, or the like.

In another aspect, embodiments of the present invention provide a system for separating an object from a patient tissue that includes a sheath having a proximal end and a distal end, and a cylindrical separator coupled with the distal end of the sheath. The separator can have an internal lumen, a proximal end, and a distal end. The distal end of the separator can define a plane, and can include plurality of teeth having separating means in perpendicular alignment with the plane or in alignment with a central longitudinal axis of the sheath. The internal lumen of the separator can define a central longitudinal axis, and an acute angle between the plane and the central longitudinal axis can be within a range from about 30 degrees to about 85 degrees.

In another aspect, embodiments of the present invention provide a system for separating an object from a patient tissue. The system can include a sheath having a distal end, and a cylindrical separator having a proximal end, a distal end, and an internal lumen that defines a central longitudinal axis. The proximal end of the separator can be coupled to the distal end of the sheath, and the distal end of the separator can include a rim that defines a plane which is not perpendicular to the central longitudinal axis of the separator, a separating mechanism disposed along a first portion of the rim, and a blunt edge disposed along a second portion of the rim. In some cases, the separating mechanism can be configured to separate the object from the tissue when the separator is rotated in one direction, but not when the separator is rotated in an opposite direction. The separating mechanism can be a cutting blade, a stripping blade, a dilating blade, or the like. In another aspect, embodiments of the present invention provide a system for separating an object from a patient tissue. The system can include a flexible shaft having a proximal end and a distal end, and a metal separator having a proximal end, a distal end, and an internal lumen that defines a central longitudinal axis. The proximal end of the separator can be coupled to the distal end of the sheath, and the distal end of the separator can include a separating means and can define a plane which is not perpendicular to the central longitudinal axis of the separator. The proximal end of the flexible shaft may be less or more flexible than the distal end of the shaft. In some cases, the distal end of the flexible shaft has a bending stiffness less than about 6 lb/in. In some cases, the flexible shaft has a torsional transmission of greater than about 0.177 pound-inch. In some cases, the flexible shaft includes a braid. In many cases, the separating mechanism is configured to separate the object from the patient tissue when the separator is rotated.

In still another aspect, embodiments of the present invention provide a system for separating an object from a patient tissue. The system includes a flexible shaft having a proximal end, a distal end, and an internal lumen having an inner diameter greater than about 0.130 inch. The shaft can have a bending stiffness of less than about 6 lb/in and a torsional transmission of greater than about 0.177 pound-inch. The system may also include a separator having a proximal end and a distal end. The proximal end of the separator can be coupled to the distal end of the sheath, the distal end of the separator can include a separating mechanism, and the separating mechanism can have a hardness greater than about B65 Rockwell. In yet another aspect, embodiments of the present invention provide a method for separating a patient tissue from an object. The method can include providing a tool that has a sheath having a proximal end and a distal end, and a separator operably coupled to the distal end of the sheath. The separator can have a proximal end, a distal end that includes a rim, a separating mechanism disposed along a first portion of the rim, a blunt edge disposed along a second portion of the rim, and an internal lumen that defines a central longitudinal axis. The method can include contacting the separating mechanism with patient tissue that is attached to the object. The method can also include rotating the separator so as to separate the tissue from the object with the separating mechanism. In some cases, the rim defines a plane that is not perpendicular to the central longitudinal axis of the separator. In some cases, the rim defines a plane that is perpendicular to the central longitudinal axis of the separator. In some cases, the separating mechanism can be configured to separate the tissue from the object when the separator is rotated in one direction, but not when the separator is rotated in an opposite direction.

In still another aspect, embodiments of the present invention provide a system for separating an object from a patient tissue. The system can include a sheath having a distal end. The system can also include a cylindrical separator having a proximal end, a distal end, and an internal lumen that defines a central longitudinal axis. The proximal end of the separator can be coupled to the distal end of the sheath, and the distal end of the separator can include a rim that defines a plane, a separating mechanism disposed along a first portion of the rim, and a blunt edge disposed along a second portion of the rim. In some cases, the plane is substantially perpendicular to the central longitudinal axis of the separator. In some cases, the plane is not substantially perpendicular to the central longitudinal axis of the separator. Optionally, an acute angle between the plane and the central longitudinal axis can be within a range from about 30 degrees to about 85 degrees.

For a fuller understanding of the nature and advantages of the present invention, reference should be had to the ensuing detailed description taken in conjunction with the accompanying drawings.

BRIEF DESCRIPTION OF THE DRAWINGS

FIG. 1 shows a system for separating an object from a patient tissue according to embodiments of the present invention.

FIG. 1A illustrates a cross section of a handle according to embodiments of the present invention.

FIG. 1B depicts a cross section of a sheath according to embodiments of the present invention.

FIG. 1C shows a cross section of a distal portion of a separating system according to embodiments of the present invention.

FIG. 2A shows a system for separating an object from a patient tissue according to embodiments of the present invention.

FIG. 2B shows a cross section of a sheath combination according to embodiments of the present invention.

DETAILED DESCRIPTION OF THE INVENTION

Figure 3:
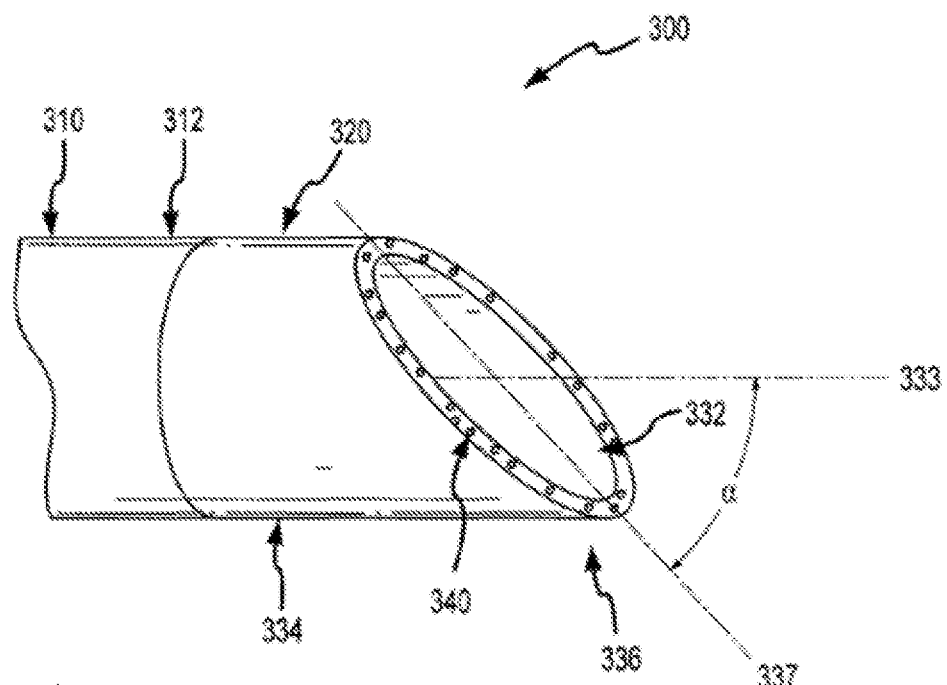
FIG. 3 illustrates a distal portion of a separating system according to embodiments of the present invention.

Embodiments of the present invention provide a mechanical sheath and cutting tip that can be safely deployed within the vascular system of a patient. Such systems include a flexible and torqueable sheath and a hard separating mechanism. A separating system can include, for example, a flexible sheath coupled with a tip, which may include a separating surface or shape. The cutting or separating surface or shape can be contacted with patient tissue, and the sheath can be rotated to effect cutting or separating of the tissue. Although the sheath may be flexible, it can also be pushable in the sense that a force applied to the proximal end of the sheath is in large part transferred to the distal end of the sheath. The sheath may also exhibit a high resistance to kinking or crushing. For example, it is possible to force the sheath into a severe bend or tortuous path without causing permanent deformation or damage to the sheath. Moreover, the sheath maintains a desired amount of torqueability, in that the a rotational force applied to a proximal end of the sheath is effectively translated to a distal end of the sheath.

A separating system can be used as an intra-operative device to free or explant a chronically implanted pacing or defibrillator lead. The system can include an inner lumen designed to allow a pacing lead and lead locking device to pass through it, as the system slides over the lead toward the distal tip of the lead in the heart. Often the system includes an outer sheath or shaft that can be used during the extraction procedure as an introducer and to support and align an inner sheath or shaft. The outer sheath can also be used as a conduit to remove the inner shaft with the extracted lead or object, and can be used as a conduit to implant a new lead or object.

Turning now to the drawings, FIG. 1 shows a system 100 for separating an object from a patient tissue according to embodiments of the present invention. System 100 can have a length A' within a range from about 25 cm to about 75 cm. In some cases, length A' is about 50 cm. System 100 includes a sheath 110 having a proximal end 112 and a distal end 114. Sheath 110 may be, for example, a braided shaft. System 110 also includes a handle 120 coupled with the proximal end 112 of sheath 110. Handle 120 can have a length B' within a range from about 4 cm to about 15 cm. In some cases, length B' is about 10 cm. System 100 also includes a cutting member or separator 130 coupled with the distal end 114 or sheath 110. In some embodiments, sheath 110 may include or be coupled with a flared exit port 140 or a similar configuration that facilitates the introduction of leads through sheath 110. In some cases, a proximal end of sheath 110 may include or be coupled with a hemostasis valve or connection to inhibit or control bleeding at the sheath proximal end. Features such as flared exit port 140 or the hemostasis valve may also be incorporated into handle 120. In use, an operator may advance sheath 110 into a patient, and while sheath is disposed within the patient, remove pacing leads or other objects from the patient. The operator may also insert new or replacement pacing leads or other objects into the patient by placing them through flared exit port 140 and into sheath 110. Thus, flared exit port 140 and sheath 110 can facilitate the implantation of a pacing lead or other object. Optionally, system 100 may include a pull wire for deflecting the distal end of the sheath. In some embodiments, a pull wire may be housed within a separate lumen of the sheath, and attached with the tip or other proximally located feature. When an operator causes the pull wire to be retracted, the pull wire causes deflection of the tip or other proximally located feature. In many cases, it is desirable to deflect a sheath top or other proximally located feature away from the wall of a vein or other body lumen. In some embodiments, sheath 110 or a portion thereof may include a braid or braiding 111. A braid may include, for example, a woven metallic or fiber layer. Often, a braid includes a group of filaments that are interwoven in a specific form, such as a cylinder or a tubular structure. A braid can be applied to the interior of sheath 110, the exterior of sheath 110, or both. In some cases, a braid may be incorporated into or integral with a sheath material. In some embodiments, a braid feature confers additional robustness to a sheath or shaft. For example, a braid may prevent or inhibit a sheath from being kinked or crushed during use.

As shown in FIG. 1A, handle 120 can have an outer diameter C' within a range from about 0.25 to about 0.95 inches. In some cases, outer diameter C' is about 0.75 inches. As shown in FIG. 1B, sheath 110 can have an inner diameter D' within a range from about 0.090 to about 0.170 inch, and an outer diameter E within a range from about 0.140 to about 0.250 inch. In some cases, inner diameter D' is about 0.130 inch and outer diameter E is about 0.155 inch. Sheath 110 can have an inner surface 116 and an outer surface 118. In some cases, inner surface 116, outer surface 118, or both, are coated with or include a slippery, smooth, or lubricious material. Exemplary hydrophilic polymer coatings or materials that may be used are produced by Surmodics, Inc. of Eden Prairie, Minn. Thus, for example, when using system 100 to remove a pacing lead from a patient, outer surface 118 passes easily through the patient's anatomy, and inner surface 116 passes easily over the pacing lead, without creating unwanted or excessive friction.

FIG. 1C illustrates cylindrical cutting member 130 and distal end 114 of sheath 110. Cylindrical cutting member 130 can include an internal lumen 132, a proximal end 134, and a distal end 136. In some cases, distal end 136 of cutting member 130 defines a plane 137. As shown here, cutting member 130 has a central longitudinal axis 133, which can be defined by, for example, internal lumen 132 of the cutting member, inner surface 116 of the shaft, or the inner or outer surface of cutting member 130. An acute angle α between plane 137 and central longitudinal axis 133 can be within a range from about 30 degrees to about 85 degrees. In some cases, angle α is about 45 degrees. Distal end 136 of cutting member 130 can include a cutting edge or surface on part of the distal end 136. In some cases, distal end 136 includes a cutting edge or surface circumscribing the entire distal end of a bevel. A cutting edge or surface can include, for example, a blade or wedge for severing tissue or for separating tissue from an object or from adjacent tissue. In some cases, a cutting edge or surface includes an abrasive substance for abrading tissue or other material. Distal end 136 may include a metal or metal alloy such as titanium, stainless steel, or a metal or alloy coated with a hard coating such as titanium oxide. Advantageously, the use of a flexible and torqueable sheath as described elsewhere herein allows an operator to advance a hard distal end 136 along an entire or substantial portion of a pacing lead, or object to be removed or separated from a patient's body, which may be located in a tortuous or labyrinthine vessel or lumen.

Sheath 110 may be motorized to rotate or coupled with a motor that induces rotation in or applies torque to the sheath. In some embodiments, sheath 110 may be motorized to move in a reciprocating motion back and forth like a clothes washer cylinder or drum. Sheath 110 can be constructed to have varying degrees of stiffness along the length of the sheath. In some cases, a distal portion or end is more flexible relative to a proximal portion or end of the sheath. For example, distal end 114 of sheath 110 may include a flexible portion approximately 5 to 15 cm in length. In some cases, sheath 110 or sections or portions thereof may be fabricated via multi-durometer construction or multi-diameter construction techniques. For example, a sheath may include a series of one or more tubes or tube-like elements of progressively reduced durometer material fused together to form a sheath of varying stiffness. Accordingly, a sheath may have one portion that exhibits a first stiffness, and a second portion that exhibits a second stiffness. In one embodiment, the hardness of the tubes or tube-like structures become progressively softer or more flexible when going from the proximal end of the sheath to the distal end of the sheath. In some embodiments, tubes or tube-like structures may have progressively smaller diameters or thicknesses when going from the proximal end of the sheath to the distal end of the sheath. Relatedly, sheath 110 can present any of a variety of braid angles. For example, a sheath or components thereof may have sections, portions, or layers having a higher angle braid angle that imparts more flexibility. Similarly, a sheath or components thereof may have sections, portions, or layers having a lower braid angle that imparts less flexibility. Sheath 110 can be configured to provide a desired torque response. For example, in some embodiments sheath 110 provides close to 1:1 torque response. Torque response can refer to the ratio of proximal rotations to distal rotations. In some embodiments, a sheath can have a torque response within a range from about 1:0.6 to about 1:1. In similar embodiments, a sheath can have a torque response within a range from about 1:0.7 to about 1:1. A sheath may also have a torque response within a range from about 1:0.8 to about 1:1. In some cases, a sheath has a torque response within a range from about 1:0.9 to about 1:1. Sheath embodiments of the present invention can advantageously provide an optimum or high torque response while retaining a high degree of flexibility, which combination is often not available with current sheath or lead removal products.

System 100 may also include a positive fixation assembly 150 or configuration for handle 120. In this way, handle 120 can be fixed or is fixable at any desired location along the length of sheath 110. In use, when sheath 110 is inserted into a patient, an operator can therefore adjust the position of handle 120 along the length of sheath 110. For example, the operator may fix handle 120 at a location that is close to the patient or near a sheath insertion point. In this way, the operator can reduce or otherwise modulate or select the amount of sheath that is present between the handle and the patient's body or insertion point. The ability to control the position of handle 120 along the length of sheath 110 allows the operator to have more easily maneuver the system 110.

If the distance between handle 120 and the patient's body or insertion point is too great, for example, the system may exhibit undesirable flexing or movement as the operator maneuvers the system. The positive fixation feature allows the handle to be movable to more proximal positions along the sheath as a lead extraction progresses.

FIG. 2A shows a system 200 for separating an object from a patient tissue according to embodiments of the present invention. System 200 includes a sheath 210 having a proximal end 212 and a distal end 214. Sheath 210 may be include from, for example, a braided shaft. System 210 also includes a handle 220 coupled with the proximal end 212 of sheath 210. System 200 also includes a cutting member or separator 230 coupled with the distal end 214 or sheath 210, and an outer sheath 240 encompassing at least a portion of sheath 210. Outer sheath 240 can have a length A' within a range from about 25 cm to about 50 cm. In some cases, length A' is about 40 cm. As shown in FIG. 2B, outer sheath 240 can have an inner diameter B' within a range from about 0.130 inch to about 0.220 inch. In some cases, inner diameter B' is about 0.170 inch. Often the outer sheath or shaft can be used during an extraction procedure as an introducer and to support and align the inner sheath or shaft. The outer sheath can also be used as a conduit to remove the inner shaft with the extracted lead or object, and can be used as a conduit to implant a new lead or object. In some embodiments, an outer sheath is left in place during a lead extraction procedure once the inner sheath and lead are removed from the patient. The outer sheath can be used as a conduit for a guidewire to facilitate the implantation of a new lead. The outer sheath distal tip can be disposed into the atrium, or retracted into the brachiocephalic vein. In some embodiments, an inner sheath and an outer sheath are advanced over a lead in an alternating "inchworm" technique. An operator may determine that a tissue obstruction is met if the inner sheath will not advance into the vessel or vein, if the inner sheath bows outward slightly when longitudinal pressure is applied, if fluoroscopy indicates that the inner sheath distal end does not advance relative to the lead body, or if fluoroscopy indicates that the inner sheath distal end is not caught on a lead electrode, a lead bend, or another lead. If an obstruction such as scar tissue is met and the inner sheath cannot be advanced, the operator may consult orthogonal fluoroscopic views to ensure that the distal tip of the inner sheath is aligned with the longitudinal axis of the lead. The operator may retract the outer sheath so that its distal end does not overlap the distal tip of the inner sheath. The operator can press the inner sheath into or against the obstruction and rotate the sheath to separate the tissue or obstruction from the lead. The outer sheath can then be advanced to a new position along the inner sheath. In some embodiments, when the lead or object is free, it is drawn into the inner sheath before the lead, the inner sheath, and the outer sheath are removed from the body. Separating systems according to the present invention are also well suited for use with lead locking devices. In some embodiments containing an inner sheath and an outer sheath, the sheaths can each have distal tips configured for a scissoring cutting action as described herein with reference to FIG. 5. In some embodiments, system 200 includes a single sheath.

FIG. 3 shows a portion of a separating system according to embodiments of the present invention. System 300 includes a shaft or sheath 310 having a distal end 312. System 300 also includes a cutting member or separator 320 coupled with distal end 312. Cutting member includes an internal lumen 332, a proximal end 334, and a distal end 336. System 300 can also include an abrasive material 340 or a separating mechanism or means disposed on or encrusted in distal end 336 of cutting member 320. In some embodiments, abrasive material 340 includes diamond chips, aluminum carbide chips, silica carbide chips, and the like. Abrasive material can be attached with distal end 336 via any of a variety of methods, including gluing, vapor deposition, embedding, and the like. In some cases, distal end or rim 336 of cutting member 320 defines a plane 337, and internal lumen 332 of the cutting member 320 defines a central longitudinal axis 333. An acute angle α between plane 337 and central longitudinal axis 333 can be about 45 degrees. In some cases, angle α is within a range from about 30 degrees to about 85 degrees. System 300 can be configured such that when distal end 336 is pressed onto patient tissue, abrasive material 340 does not cut or sever the tissue, but when distal end is pressed onto patient tissue and sheath 310 or cutting member 320 is rotated about central longitudinal axis 333, abrasive material 340 acts to cut or sever the tissue.

Figure 4:
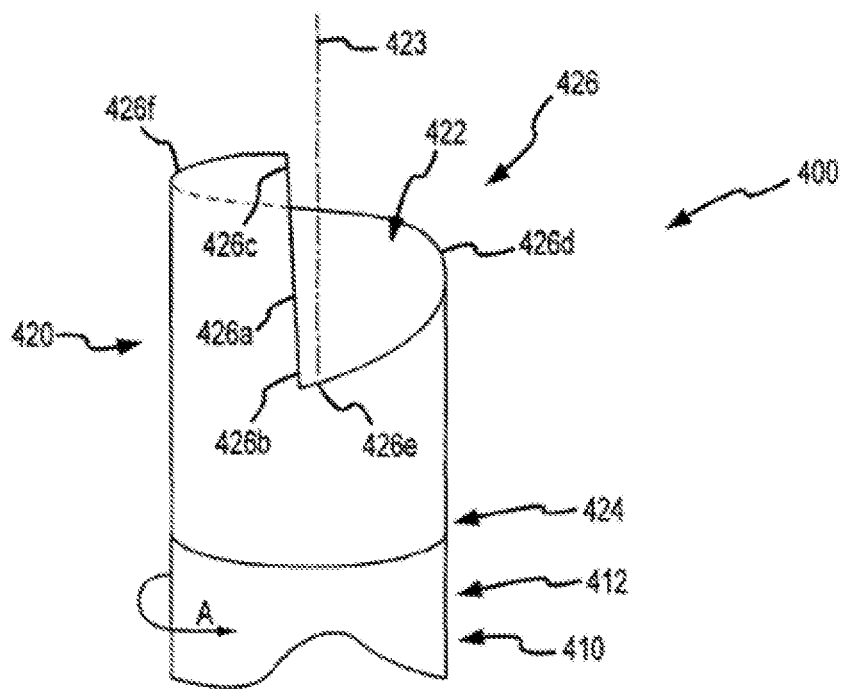
FIG. 4 illustrates a distal portion of a separating system according to embodiments of the present invention.

FIG. 4 shows a portion of a separating system according to embodiments of the present invention. System 400 includes a sheath 410 having a distal end 412. System 400 also includes a cutting member or separator 420 coupled with distal end 412. Cutting member includes an internal lumen 422, a proximal end 424, and a distal end or rim 426. Internal lumen 422 defines a central longitudinal axis 423. Distal end 426 of cutting member 420 includes a separating means or mechanism such as a cutting edge 426a aligned with central longitudinal axis 423, and cutting edge or blade 426a has a proximal end 426b and a distal end 426c. Distal end 426 of cutting member 420 also includes a distal edge 426d having a proximal end 426e that joins or meets with the cutting edge proximal end 426b, and a distal end 426f that joins or meets with cutting edge distal end 426c. Separating mechanism 426a can present any desired profile for separating tissue. As shown here, separating mechanism 426a defines a substantially straight edge profile that extends between cutting edge distal end 426c and cutting edge proximal end 426b. In some embodiments, the profile provided by separating mechanism 426a between cutting edge distal end 426c and cutting edge proximal end 426b presents an arc, or a convex or concave contour. In some cases, the profile may have an irregular contour. In addition, leading edge 426c can have a rounded profile to prevent tissue penetration when the sheath is advanced longitudinally. Relatedly, separating mechanism 426a may also provide a beveled edge, similar to blade 814 as described with reference to FIG. 5B. Distal edge 426d often presents or includes a spiral or helical contoured portion or shape. Any of a variety of materials can be used in the manufacture of a cutting element. For example, a cutting element may include a metal or metal alloy such as titanium, stainless steel, or a metal coated with a hard coating such as titanium oxide. In some embodiments, cutting member 420 is configured to cut only when rotated one direction, when blade 426a presents a leading edge, as indicated by arrow A.

Figure 5:
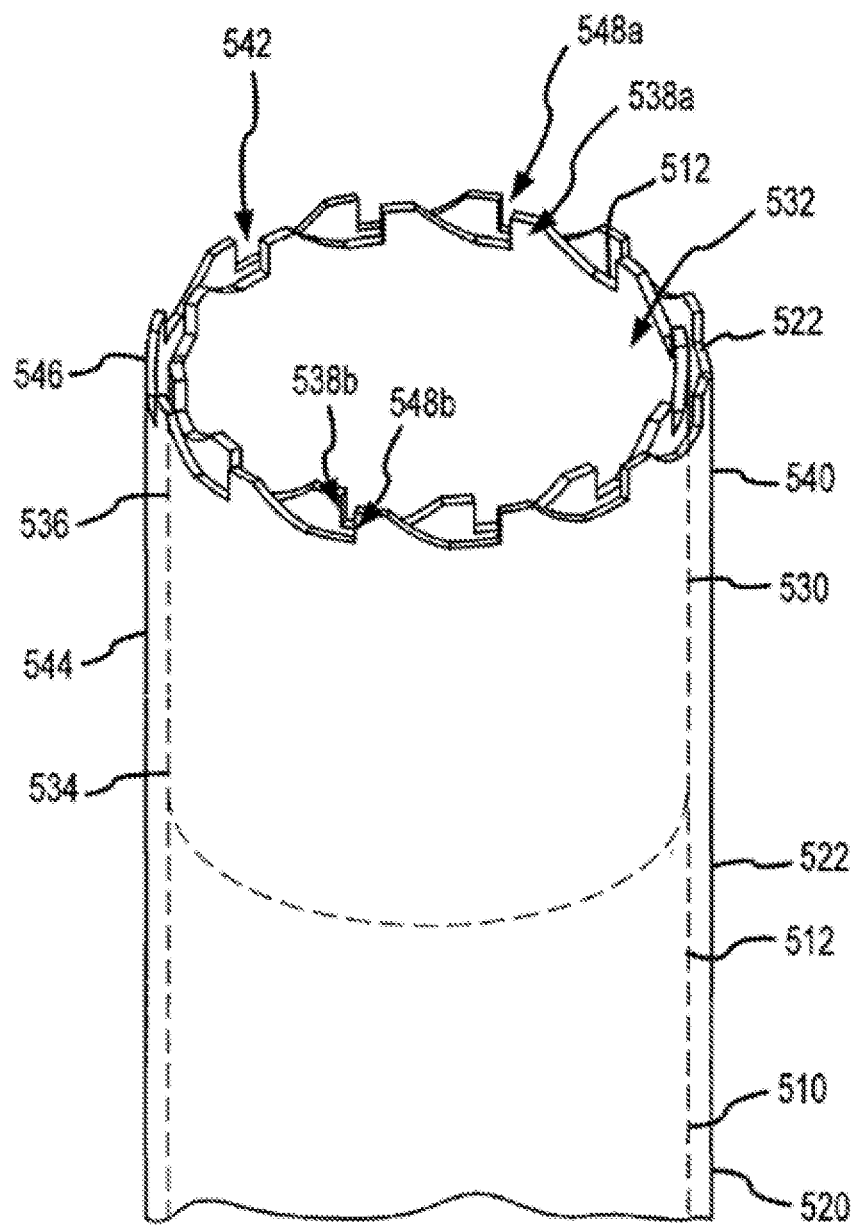
FIG. 5 illustrates a distal portion of a separating system according to embodiments of the present invention.

FIG. 5 shows a portion of a separating system according to embodiments of the present invention. System 500 includes an internal sheath 510 having a distal end 512, and an external sheath 520 having a distal end 522. System 500 also includes an internal cutting member or separator 530 coupled with distal end 512. Internal cutting member 530 includes an internal lumen 532, a proximal end 534, and a distal end or rim 536. In some cases, internal cutting member is cylindrical in shape. Distal end 536 of internal cutting member 530 can include one or more cutting blades 538a,b. System 500 also includes an external cutting member or separator 540 coupled with distal end 522. External cutting member 540 includes an internal lumen 542, a proximal end 544, and a distal end 546. In some cases, external cutting member is cylindrical in shape. Distal end 546 of external cutting member 540 can include one or more cutting blades or separating means or mechanism 548a,b. As shown here, internal cutting member 530 is disposed at least partially within external cutting member 540, and internal and external cutting members 530, 540 are configured for relative rotational movement so that blade pairs can form scissors or clippers. For example, blade 538a and blade 548a can be brought together or toward each other in a shearing or clipping fashion. In some embodiments, each of the internal and external sheaths have distal metal bands. Each band can be serrated in such a way that each band forms one or more blades of one or more scissor pairs, where one blade of each scissor pair is located on each band. In use, the internal and external sheaths can be rotated relative to one another to close the scissor pairs and produce a cutting action. In addition to or instead of the cutting action, rotation or advancement of one or both of the sheaths can operate to perform a dilating or stripping action. In many cases, however, the actuation of the distal end of the system provides a primarily cutting or clipping action.

Figure 6:
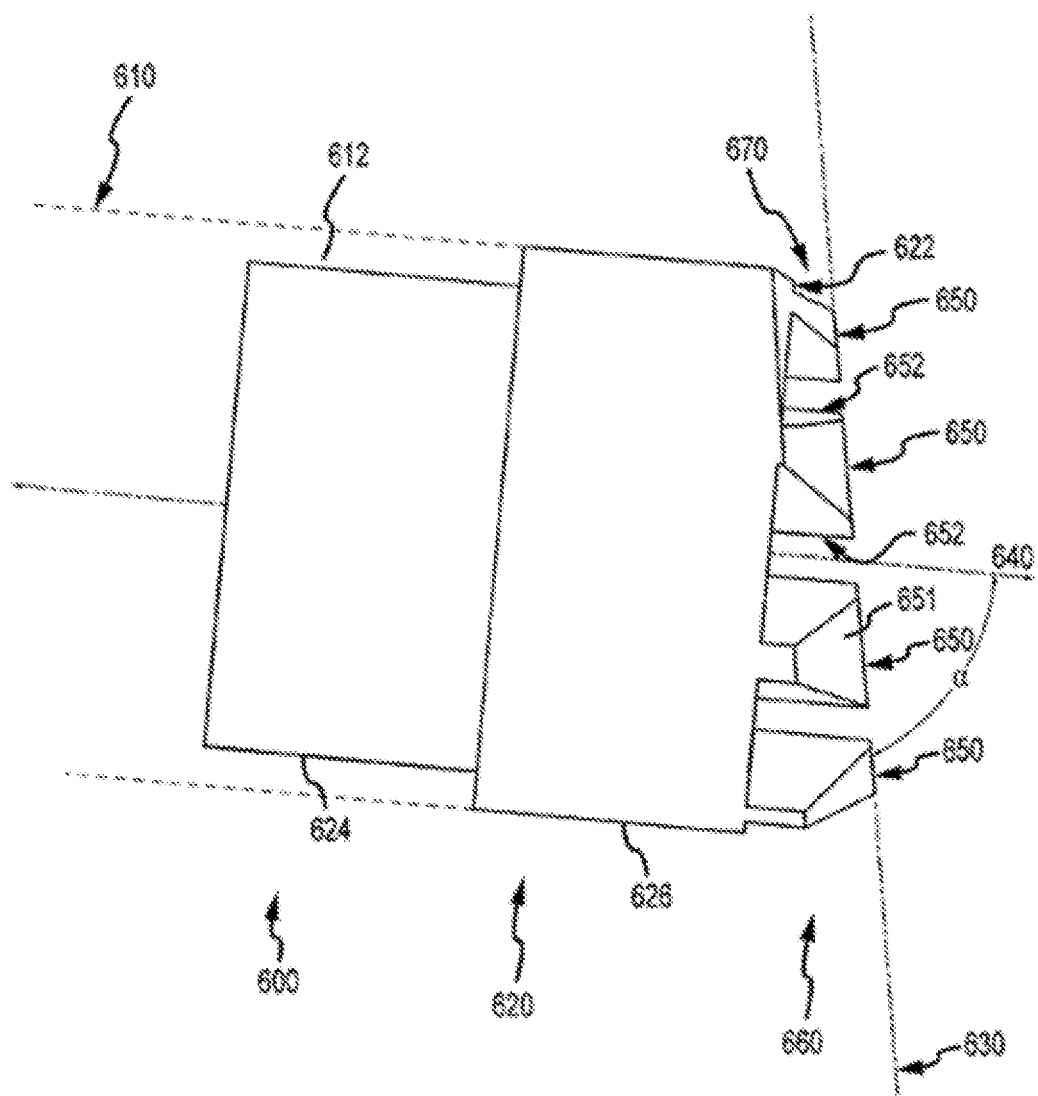
FIG. 6 depicts a distal portion of a separating system according to embodiments of the present invention.
Figure 6A:
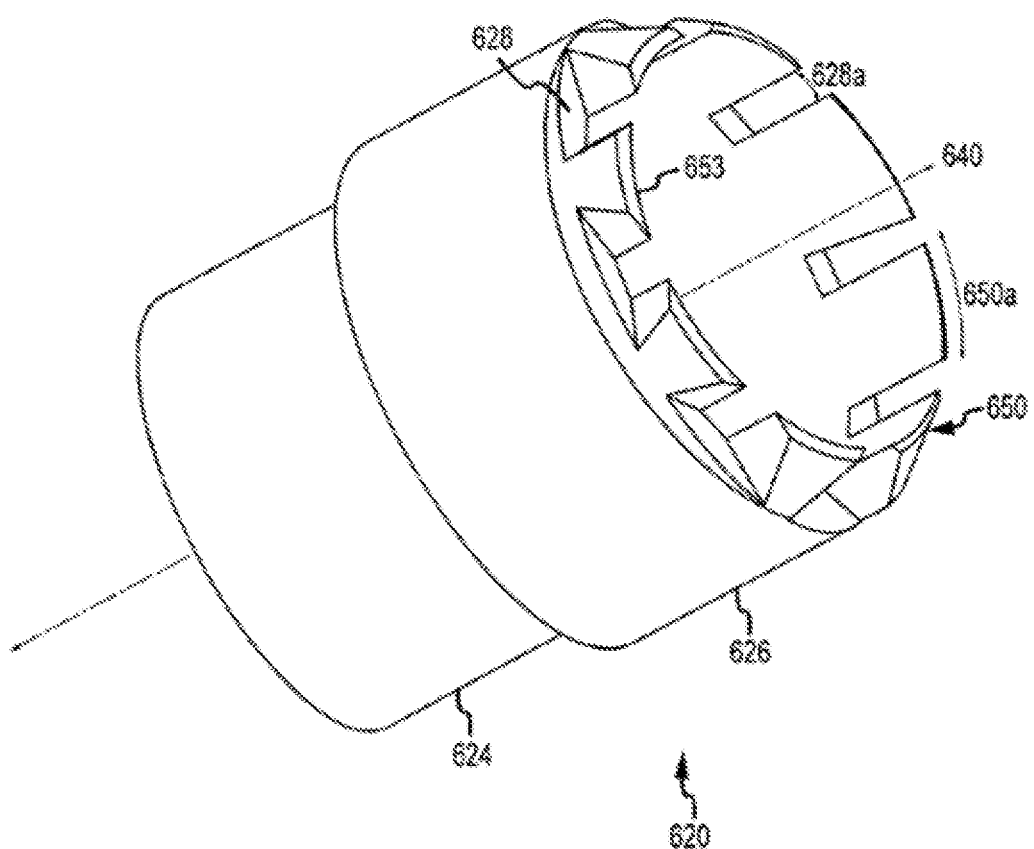
FIG. 6A depicts a distal portion of a separating system according to embodiments of the present invention.

FIG. 6 shows a system 600 for cutting tissue in a patient according to embodiments of the present invention. System 600 includes a sheath 610 having a distal end 612, and a cutting member 620 coupled with distal end 612. In some cases, cutting member 620 provides a cylindrical shape. Cutting member 620 includes an internal lumen 622, a proximal end 624, and a distal end or rim 626. In some cases, distal end 626 of cutting member 620 defines a plane 630, and internal lumen 622 of the cutting member 620 defines a central longitudinal axis 640, wherein an acute angle α between plane 630 and central longitudinal axis 640 is within a range from about 45 degrees to about 90 degrees. In some cases, angle α is within a range from about 60 degrees to about 85 degrees. In embodiments where there is such an angle, distal end 626 of cutting member 620 may present a leading edge 660 and a trailing edge 650. For example, leading edge 660 can be disposed toward the cutting member distal end 626 and trailing edge 670 can be disposed toward the cutting member proximal end 624. In some cases, distal end 626 of cutting member 620 includes a plurality of teeth or serrations 650. Teeth 650 can have cutting edges or blades 652 along the side walls of the teeth. The top surface or peripheral lateral surfaces 651 of the teeth can be rounded or smooth. The inner diameter 653 of each tooth may present a sharp edge. In some cases, cutting edges 652 are in perpendicular alignment with plane 630 or with a plane defined by face 628. In some cases, cutting edges 652 are in directional alignment with a central longitudinal axis defined by the cutting member or separator. In some cases, cutting or separating edges 652 are in directional alignment with a central longitudinal axis defined by the sheath. As shown in FIG. 6A, distal end 626 of cutting member 620 may present a circular face 628, and a plurality of teeth or crests 650 are disposed circumferentially around the face. There is a substantially equivalent or equivalent arc spacing 628a between each tooth 650, and each tooth presents a similar or equivalent width arc width 650a along inner diameter edge 653. In some embodiments, the arc spacing 628a between teeth 650 may be unequal. In some embodiments, the arc width 650a may vary among different teeth 650. In some cases, teeth may be present at one portion of the face 628, and absent from another portion of the face 628. For example, in some embodiments, leading edge 660 may include one or more teeth, whereas trailing edge 670 may contain no teeth. Relatedly, in some embodiments one portion of the face may contain more teeth than another similar-sized portion of the face.

Figure 7A:
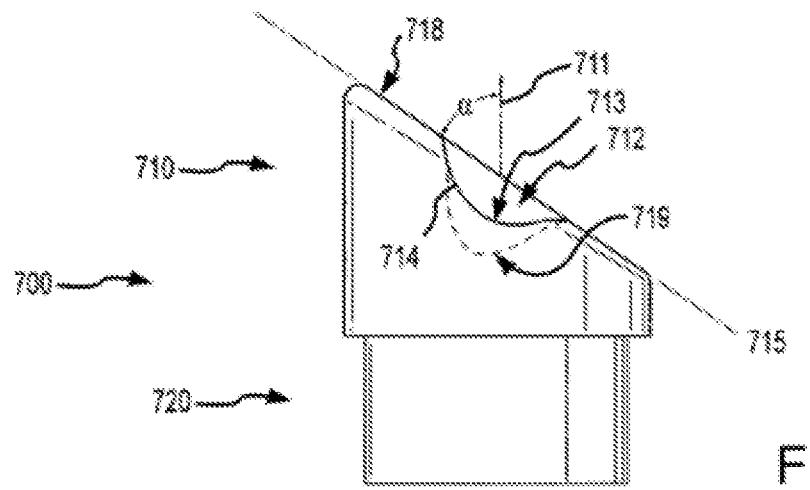
FIGS. 7A-7D show aspects of a separator according to embodiments of a present invention.
Figure 7B:
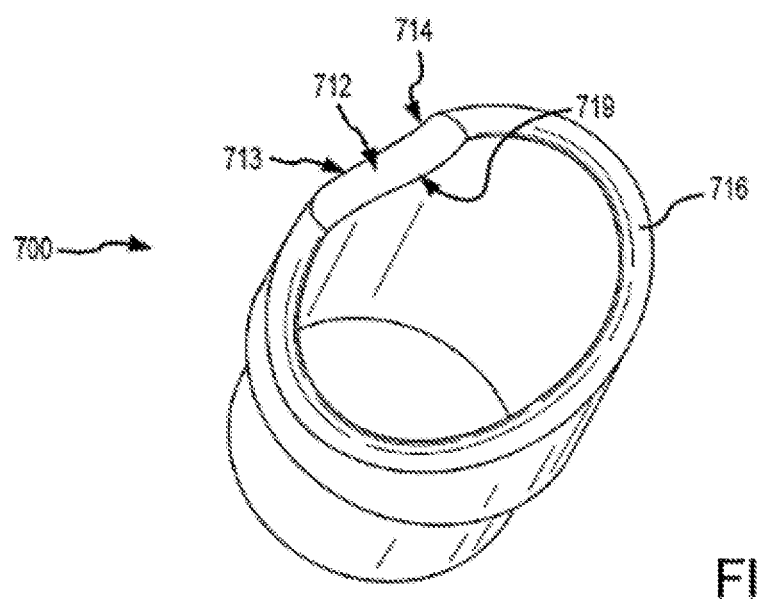
Figure 7C:
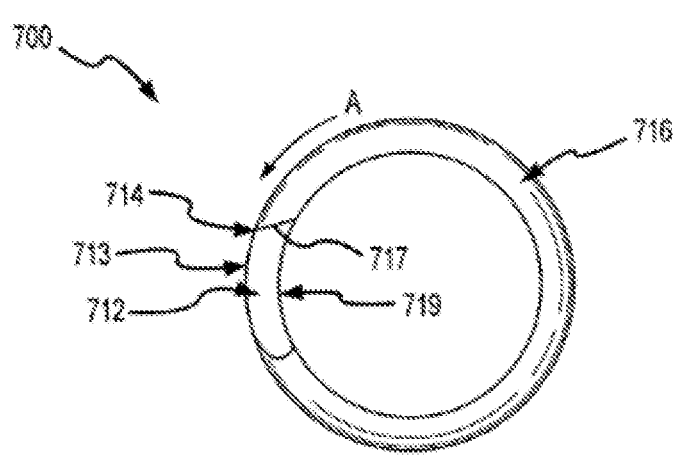
Figure 7D:
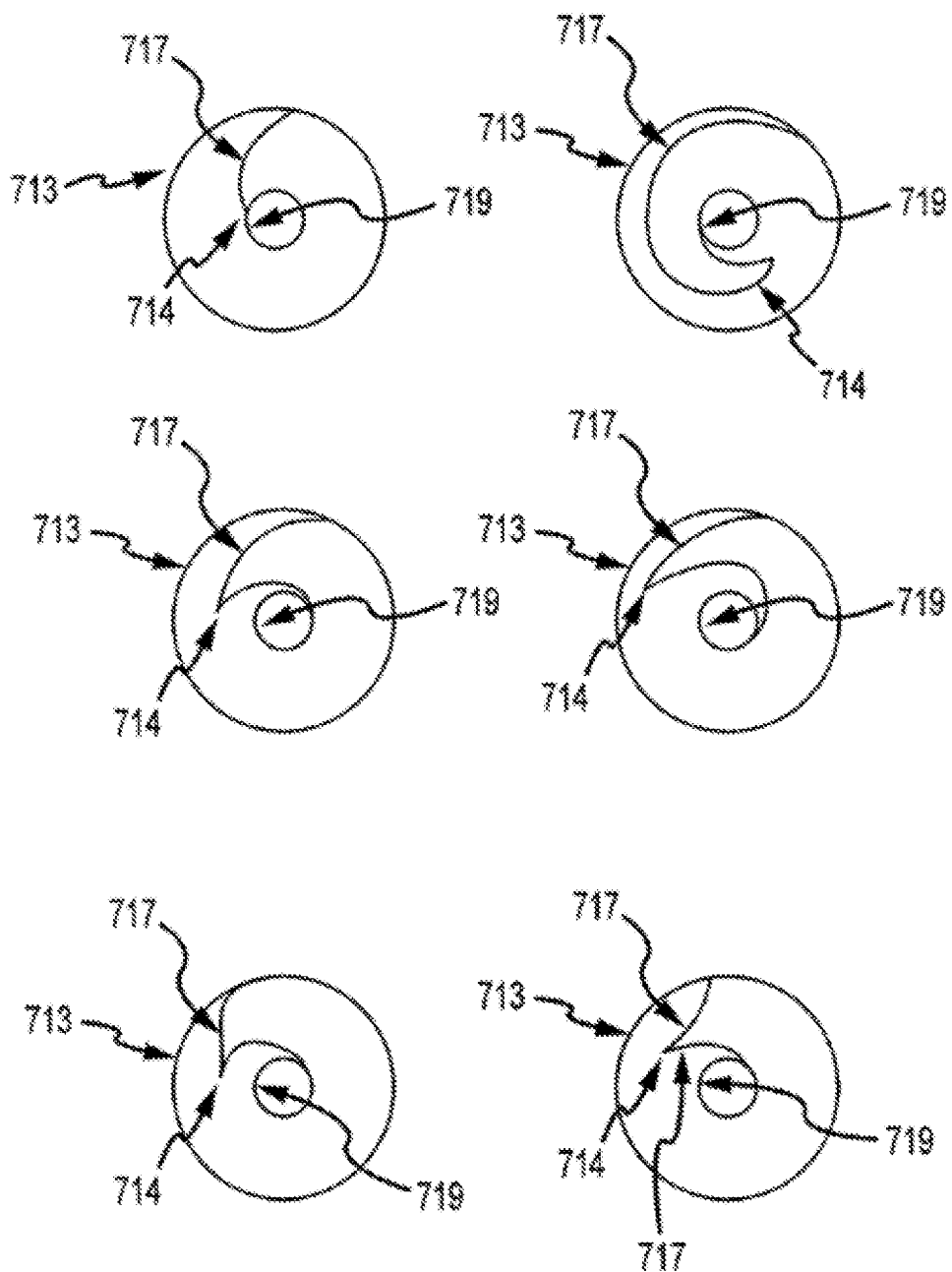
Figure 7E:
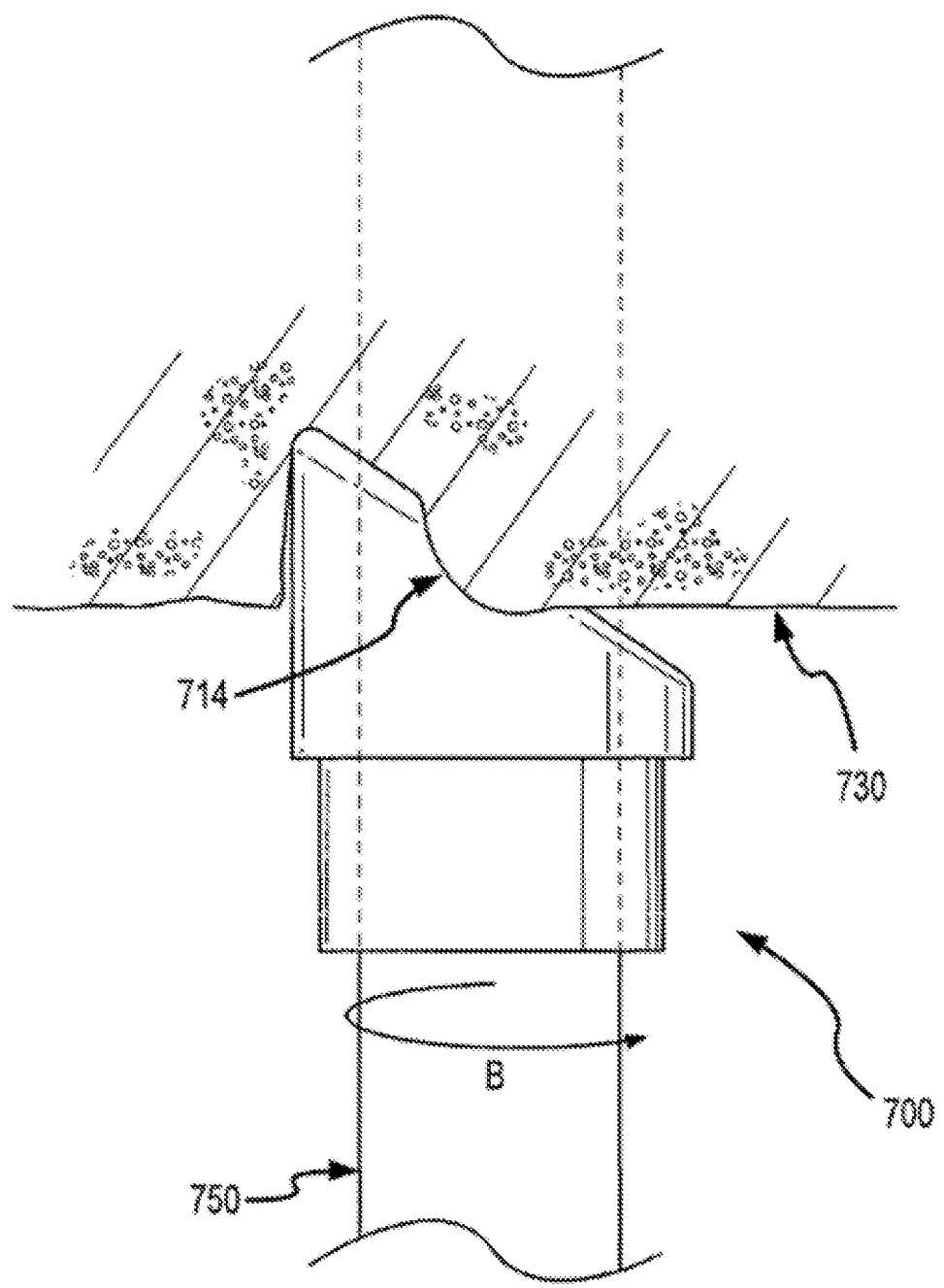
FIG. 7E shows a distal portion of a separating system in a method of use according to embodiments of the present invention.

FIGS. 7A-7D illustrate a cutting member or separator 700 according to embodiments of the present invention. As shown in the side view provided by FIG. 7A, cutting member 700 includes a distal end or rim 710 and a proximal end 720. Distal end 710 is beveled and defines a plane 715. In some embodiments, plane 715 may be skew or not perpendicular to central longitudinal axis 711. For example, there may be an acute angle α between plane 715 and axis 711 within a range from about 30 degrees to about 85 degrees. Axis 711 can be a central longitudinal axis defined by an internal lumen of cutting member 700. Distal end 710 also includes a recess 712 having a blade or separating mechanism 714. As shown in the perspective view provided by FIG. 7B, distal end 710 also includes a rounded or smooth surface 716. Distal end 710 can also include a distal tip 718 that is rounded or smooth. Often, distal tip 718 is somewhat blunted, and does not present a sharp point or a leading cutting edge when cutting member 700 is advanced. In use, distal tip 718 of cutting member 700 can be pressed lightly against a patient tissue without severing the tissue. Cutting member 700 can be rotated in the direction indicated by the arrow A shown in FIG. 7C to advance the leading edge of blade 714. In contrast to rounded or smooth surface 716, recess 712 can present a scooped or beveled surface that presents a sharp, acute, or knifelike blade 714. Outer diameter 713 of recess 712 can be disposed proximal relative to inner diameter 719 of recess 712. Blade 714 can be disposed along the outer diameter 713 of recess 712. As shown in FIG. 7D, blade 714 may also be disposed along inner diameter 719, or between outer diameter 713 and inner diameter 719, and may define any suitable combination of convex, concave, or curved bevel surface 717. FIG. 7E provides a side view of cutting member 700 in use, where cutting member 700 is rotated in the direction indicated by arrow B, so that blade 714 presses against and cuts patient tissue 730. In this manner, tissue 730 can be severed or separated from an object such as a pacing lead 750.

Figure 8A:
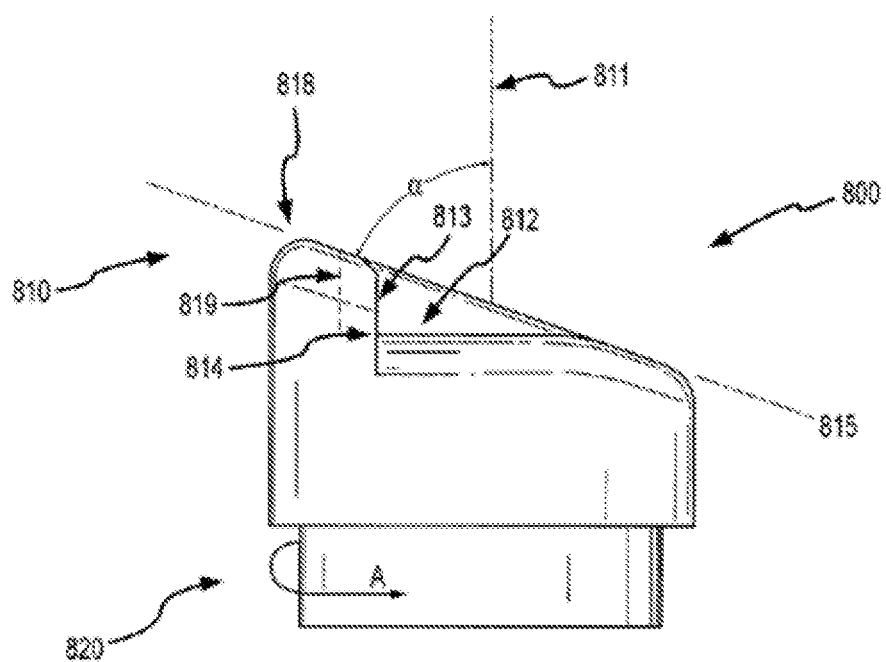
FIGS. 8A and 8B show aspects of a separator according to embodiments of a present invention.
Figure 8B:
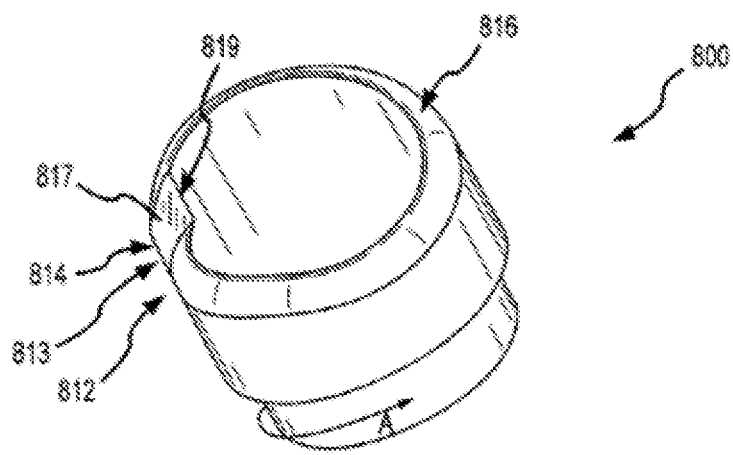

FIGS. 8A and 8B illustrate a cutting member or separator 800 according to embodiments of the present invention. As shown in the side view provided by FIG. 8A, cutting member 800 includes a distal end or rim 810 and a proximal end 820. Distal end 810 is beveled and defines a plane 815. In some embodiments, plane 815 may be skew or not perpendicular to central longitudinal axis 811. For example, there may be an acute angle α between plane 815 and axis 811 within a range from about 30 degrees to about 85 degrees. Axis 811 can be a central longitudinal axis defined by an internal lumen of cutting member 800. Distal end 810 also includes a notch 812 and a blade or separating means or mechanism 814. As shown in the perspective view provided by FIG. 8B, distal end 810 also includes a rounded or smooth surface 816. Often, distal tip 818 is somewhat blunted, and does not present a sharp point or a leading cutting edge when cutting member 800 is advanced. In use, a distal tip 818 of cutting member 800 can be pressed lightly against a patient tissue without severing the tissue. In a manner similar to that described with reference to cutting member 700, cutting member 800 can be rotated so as to cut patient tissue. Cutting member 800 can be rotated in the direction indicated by the arrow A shown in FIG. 8B to advance the leading edge of blade 814. In some embodiments, cutting member 800 is configured to cut only when rotated one direction, when blade 814 presents a leading edge. In contrast to rounded or smooth surface 816, notch 812 can present a scooped or beveled surface that presents a sharp, acute, or knifelike blade 814. Outer diameter 813 of notch 812 can be disposed proximal relative to inner diameter 819 of recess 812. Blade 814 can be disposed along the outer diameter 813 of notch 812. In a manner similar to that described above with reference to blade 714, blade 814 may also be disposed along inner diameter 819, or between outer diameter 813 and inner diameter 819, and may define any suitable combination of convex, concave, or curved bevel surface 817.

Figure 9A:
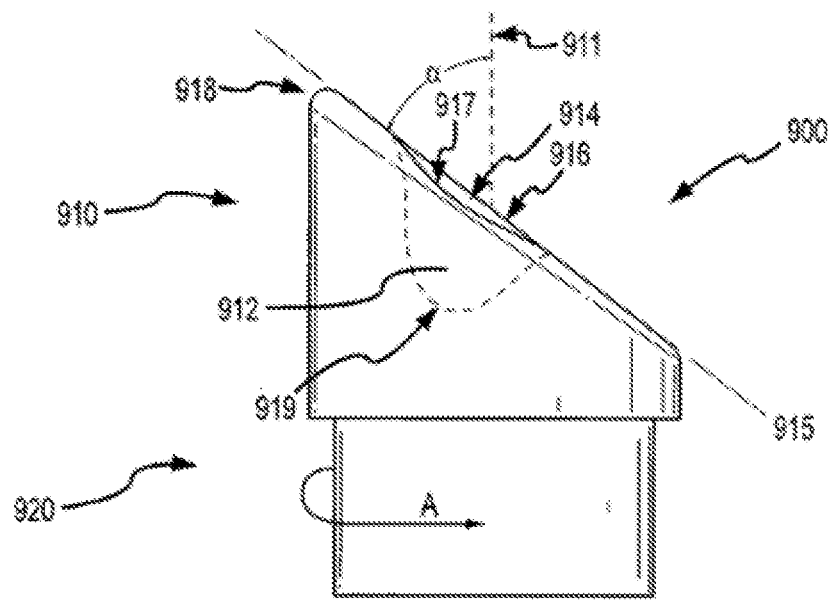
FIGS. 9A and 9B show aspects of a separator according to embodiments of a present invention.
Figure 9B:
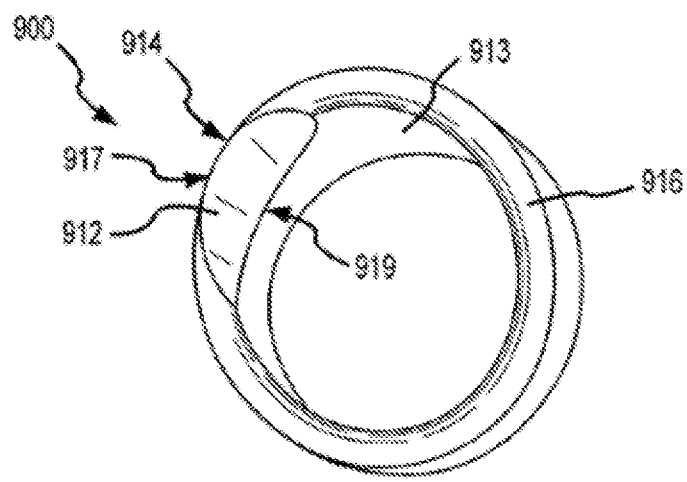

FIGS. 9A and 9B show a cutting member or separator 900 according to further embodiments of the present invention. As shown in the side view provided by FIG. 9A, cutting member 900 includes a distal end or rim 910 and a proximal end 920. Distal end 910 is beveled and defines a plane 915. In some embodiments, plane 915 may be skew or not perpendicular to central longitudinal axis 911. For example, there may be an acute angle α between plane 915 and axis 911 within a range from about 30 degrees to about 85 degrees. Axis 911 can be a central longitudinal axis defined by an internal lumen of cutting member 900. As shown in the perspective view provided by FIG. 9B, distal end 910 also includes a rounded or smooth surface 916, and a depression 912 in an interior surface 913 of cutting member 900. Depression 912 presents a blade or separating means or mechanism 914 for use in cutting or separating patient tissue. In use, a distal tip 918 of cutting member 900 can be pressed lightly against a patient tissue without severing the tissue. In a manner similar to that described with reference to cutting member 700, cutting member 900 can be rotated so as to cut patient tissue. Cutting member 900 can be rotated in the direction indicated by the arrow A shown in FIG. 9A to advance the leading edge of blade 914. In contrast to rounded or smooth surface 916, depression 912 can present a scooped or beveled surface that presents a sharp, acute, or knifelike blade 914. Outer diameter 917 of depression 912 can be disposed proximal relative to inner diameter 919 of depression 912. Blade 914 can be disposed along the outer diameter 913 of depression 912, or blade 914 may be at least partially disposed between outer diameter 913 and inner diameter 919. In a manner similar to that described above with reference to blade 714, blade 914 may also be disposed along inner diameter 919.

Figure 10A:
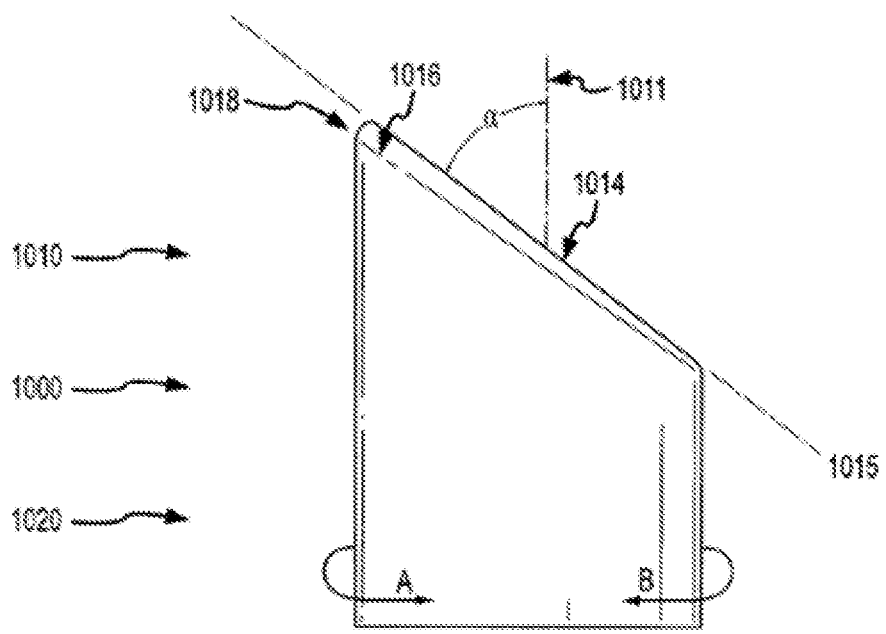
FIGS. 10A and 10B show aspects of a separator according to embodiments of a present invention.
Figure 10B:
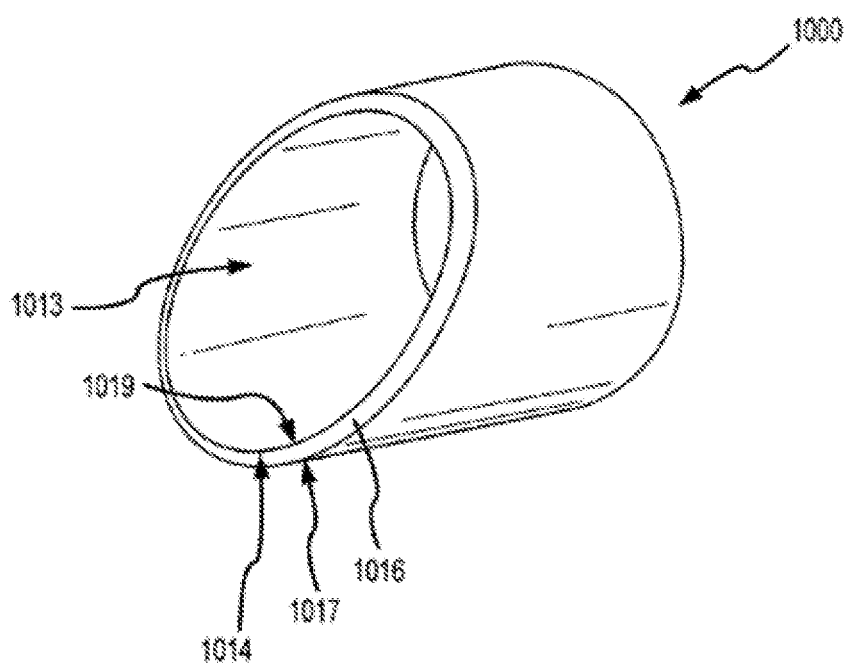

FIGS. 10A and 10B show a cutting member or separator 1000 according to embodiments of the present invention. As shown in the side view provided by FIG. 10A, cutting member 1000 includes a distal end or rim 1010 and a proximal end 1020. Distal end 1010 is beveled and defines a plane 1015. In some embodiments, plane 1015 may be skew or not perpendicular to central longitudinal axis 1011. For example, there may be an acute angle α between plane 1015 and axis 1011 within a range from about 30 degrees to about 85 degrees. Axis 1011 can be a central longitudinal axis defined by an internal lumen of cutting member 1000. As shown in the perspective view provided by FIG. 10B, distal end 1010 also includes rounded or smooth surface 1016, and a blade or sharp surface 1014 that extends at least partially around the periphery of distal end 1010, where blade or separating mechanism or means 1014 can be used for cutting or separating patient tissue. Often, blade 1014 is disposed at or near an inner surface 1013 of cutting member 1000. In some cases, blade 1014 can include an edge of inner surface 1013. In use, a distal tip 1018 of cutting member 1000 can be pressed lightly against a patient tissue without severing the tissue. In a manner similar to that described with reference to cutting member 700, cutting member 1000 can be rotated so as to cut patient tissue. Cutting member 1000 can be rotated in the direction indicated by the arrow A shown in FIG. 10A, or in the direction indicated by arrow B, to advance the leading edge of blade 1014. As shown here, rounded or smooth surface 1016 may be continuous with a sharp, acute, or knifelike blade 1014. Surface 1016 may be disposed at or toward outer diameter 917 of cutting member 1000, and blade 1014 may be disposed at or toward inner diameter 1019 of cutting member 1000. In some cases, blade 1014 may be disposed distal to smooth surface 1016, and in some cases blade 1014 may be disposed proximal to smooth surface 1016. In some embodiments, cutting or separating mechanism 1014 can be disposed along the inner diameter 1019 of separator 1000. Thus, in use the cutting or separating mechanism 1014 can be kept away from a vessel wall or other portion of the patient's body. Separating mechanism 1014 can also extend circumferentially about the distal end of separator 1000, and thus can provide a cutting or separating action when separator 1000 is advanced longitudinally, as well as when separator 1000 is rotated in either direction.

Figure 11A:
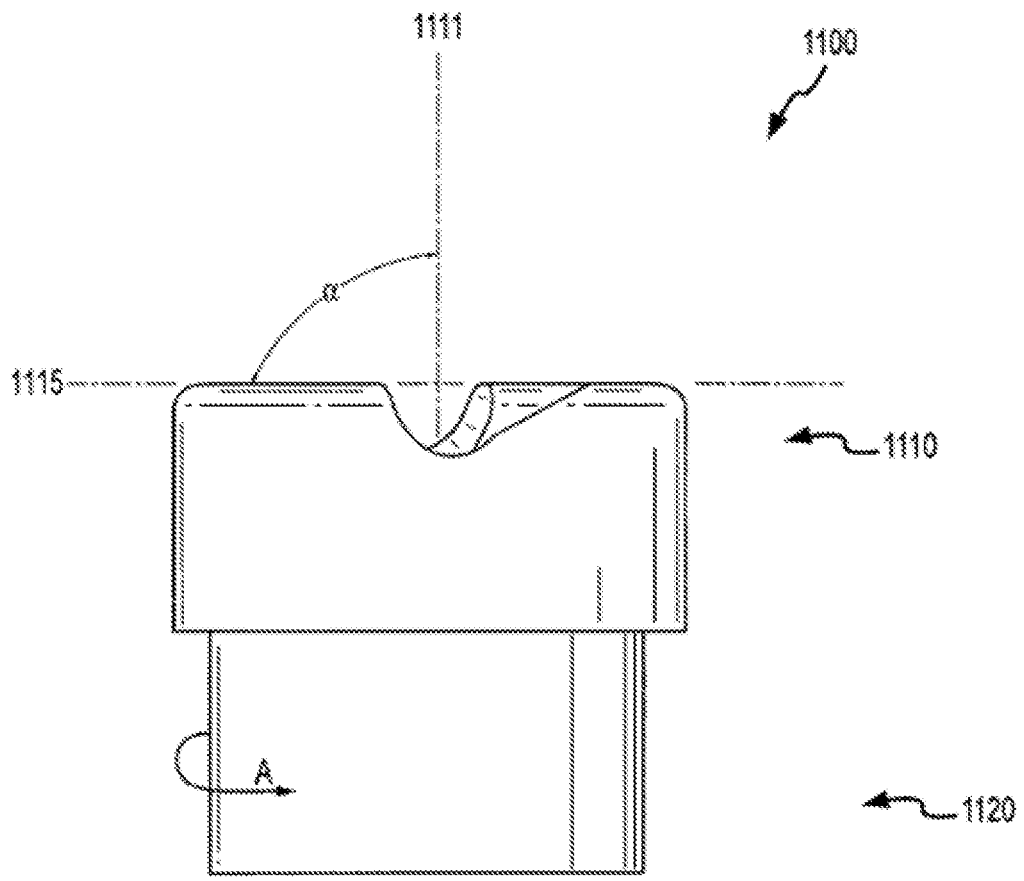
FIGS. 11A and 11B show aspects of a separator according to embodiments of a present invention.
Figure 11B:
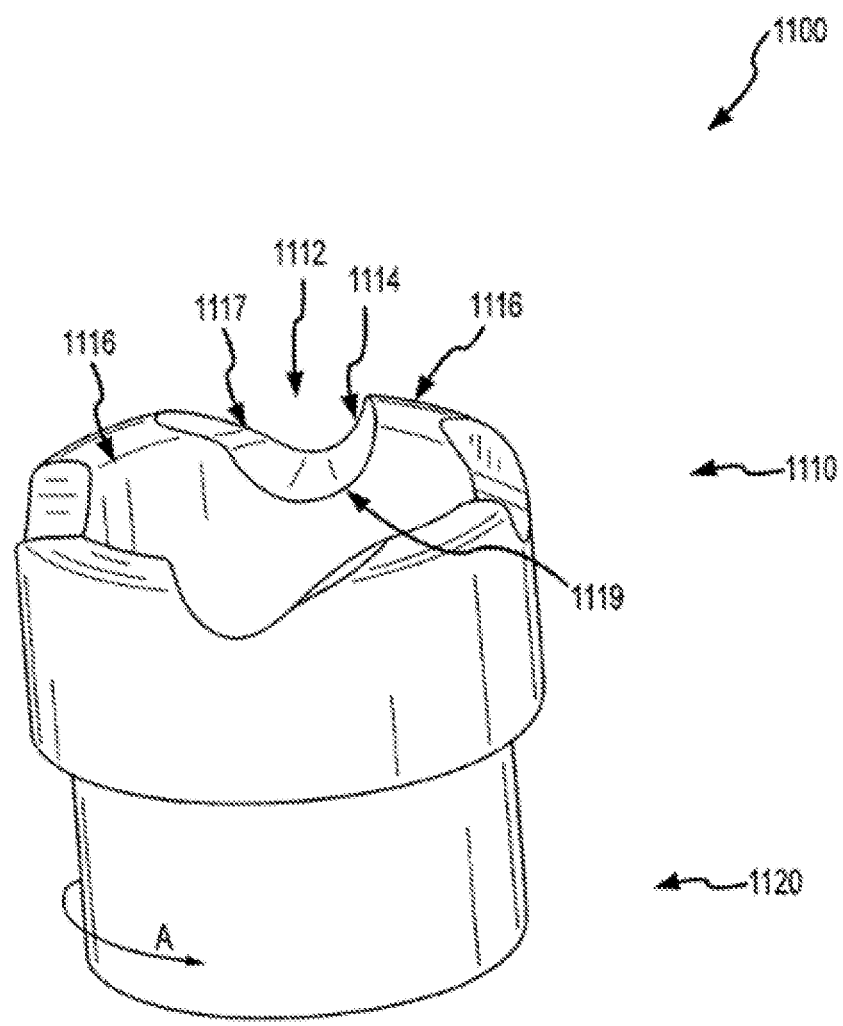

FIGS. 11A and 11B show a cutting member or separator 1100 according to embodiments of the present invention. As shown in the side view provided by FIG. 11A, cutting member 1100 includes a distal end or rim 1110 and a proximal end 1120. Distal end 1110 defines a plane 1115 that is substantially perpendicular or perpendicular to a central longitudinal axis 1111 of cutting member 1100, and thus angle α is 90 degrees or about 90 degrees. In some embodiments, plane 1115 may be skew or not perpendicular to central longitudinal axis 1111. For example, there may be an acute angle between plane 1115 and axis 1111 within a range from about 30 degrees to about 85 degrees. As shown in the perspective view provided by FIG. 11B, distal end 1110 also includes at least one rounded or smooth surface 1116, and at least one recess 1112, where recess 1112 can provide a blade or separating mechanism or means 1114. In use, a distal tip 1118 of cutting member 1100 can be pressed lightly against a patient tissue without severing the tissue. In a manner similar to that described with reference to cutting member 700, cutting member 1100 can be rotated so as to cut patient tissue. Cutting member 1100 can be rotated in the direction indicated by the arrow A shown in FIG. 11B to advance the leading edge of blade 1114. In contrast to rounded or smooth surface 1016, recess 1112 can present a scooped or beveled surface that presents a sharp, acute, or knifelike blade 1114. Outer diameter 1117 of recess 1112 can be disposed proximal relative to inner diameter 1119 of recess 1112. Blade 1114 can be disposed along the outer diameter 1117 of recess 1112. In a manner similar to that described above with reference to blade 714, blade 1114 may also be disposed along inner diameter 1119, or between inner diameter 1119 and outer diameter 1117.

Figure 12:
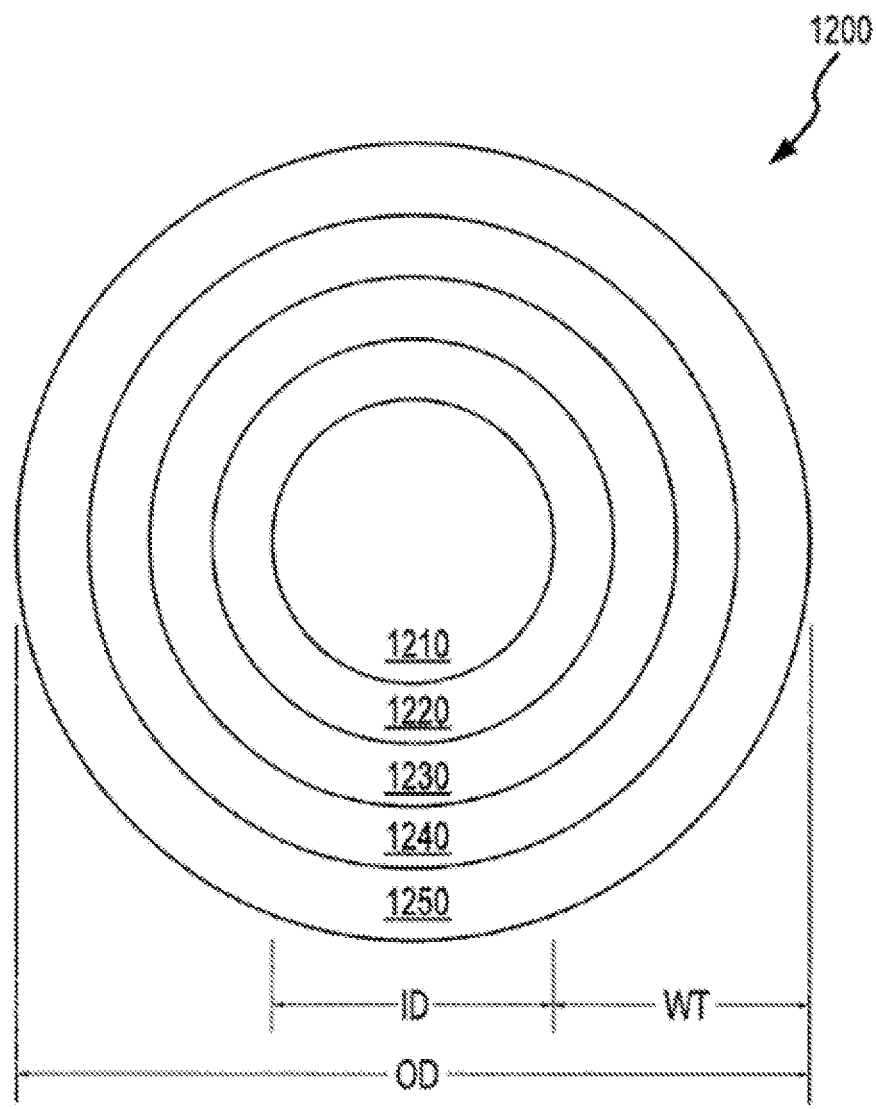
FIG. 12 illustrates a cross section of a sheath according to embodiments of the present invention.

FIG. 12 illustrates a cross section of a flexible sheath or shaft according to embodiments of the present invention. Shaft 1200 includes an inner lumen 1210, an inner layer 1220, a central layer 1230, a braid layer 1240, and an outer layer 1250. In some embodiments, an inner diameter ID of shaft 1200 is within a range from about 0.147 inch to about 0.187 inch. Optionally, inner diameter ID can be about 0.167 inch. In some embodiments, an outer diameter OD of shaft 1200 is within a range from about 0.175 inch to about 0.215 inch. Optionally, outer diameter OD can be about 0.195 inch. Shaft 1200 may have a total wall thickness WT within a range from about 0.011 inch to about 0.068 inch. Inner layer 1220 may include a fluoropolymer such as fluorinated ethylene propylene (FEP) or polytetrafluoroethylene (PTFE). Inner layer 1220 can have a wall thickness of about 0.002 inch. Central layer 1230 may include a thermoplastic elastomer such as Pebax (polyether bloc amide), with a durometer of about 25. Central layer 1230 can have a wall thickness of about 0.002 inch. Braid layer 1240 can include a 304 stainless steel ribbon having a thickness of about 0.001 inch and a width of about 0.004 inch. Braillayer 1240 can have a wall thickness of about 0.002 inch, due to two overlapping layers of the 0.001 inch thick ribbon. Outer layer 1250 can include a thermoplastic elastomer such as Pebax® with a durometer of about 69. In some embodiments, the braid is a 16 strand braid having a 35 Pic count (crossings per inch). The braid may present 28 percent coverage (surface area) and a braid angle of about 67.8 degrees. Such sheath configurations provide for a very flexible construction that retains effective torque properties.

In some embodiments, shaft 1200, in combination with a separator, can be dimensioned to remove pacing leads up to 13 French (0.170 inch) in diameter. The shaft can have a bending stiffness of less than about 6 pounds per inch (lb/in), and a torsional stiffness greater than about 0.177 pound inch (lb-in). The separator can include a separating mechanism having a hardness greater than about B65 Rockwell. The separating mechanism hardness can be measured by the Rockwell scale, a standard scale used to grade metals. Table 1 provides a comparison between an exemplary shaft embodiment and other commonly used lead extraction shafts.

TABLE 1

| Test Number | Bending Stiffness (lbf/in) | Torsional Transmission (lb-in) 90° | Torsional Transmission (lb-in) 180° |
|---|---|---|---|
| Shaft | 1 | 3.674 | 0.266 | 0.434 |
| 0.195 inch OD | 2 | 3.681 | | |
| 0.169 inch ID | 3 | 3.81 | | |
| Commercial sheath 1 | 1 | 13.643 | 0.637 | 0.708 |
| 0.18 inch OD | 2 | 15.19 | | |
| 0.151 inch ID | 3 | 14.626 | | |
| Commercial sheath 2 | 1 | 6.662 | 0.531 | 0.903 |
| 0.205 inch OD | 2 | 7.071 | | |
| 0.169 inch ID | 3 | 7.006 | | |
| Commercial sheath 3 | 1 | 6.965 | 0.363 | 0.531 |
| 0.136 inch OD | 2 | 6.998 | | |
| 0.109 inch ID | 3 | 6.729 | | |
| Commercial sheath 4 | 1 | 3.31 | 0.150 | 0.186 |
| 0.153 inch OD | 2 | 3.292 | | |
| 0.112 inch ID | 3 | 3.284 | | |
| Commercial sheath 5 | 1 | 13.009 | | |
| 0.205 inch OD | 2 | 13.457 | | |
| 0.168 inch ID | 3 | 13.932 | | |
| Commercial sheath 6 | 1 | 2.983 | | |
| 0.153 inch OD | 2 | 3.014 | | |
| 0.112 inch ID | 3 | 3.012 | | |

Table 1 indicates that embodiments of the present invention provide a sheath having bending properties similar to a smaller commonly available sheath. However, the present sheath can be sized to accommodate a lead or other object having a large diameter, while still retaining desirable torque properties. Moreover, embodiments of the present invention provide a system that includes a flexible and torqueable sheath and a hard separating mechanism.

Bending stiffness can be defined as the slope of the force/deflection curve pursuant to a flexural test such as ASTM D790 (e.g. 3 point bend test with 3 inch span length). Embodiments of the present invention provide sheaths having a bending stiffness of less than about 6 pound force per inch. Torsional transmission can be defined as the resulting torque load (e.g. in Newton-centimeters) transmitted to a distal end of a sheath while rotating a proximal end of the sheath a given amount (e.g. 90 degrees). The torsional transmission values provided in Table 1 correspond to a span (tube) length of 12 inches. An exemplary separating system may therefore include a flexible shaft having an inner diameter greater than about 0.130 inch and a bending stiffness of less than about 6 lb/in. The shaft can have a torsional transmission of greater than about 0.177 lb-in. The system can also include a separating mechanism having a hardness greater than about B65 Rockwell.

In addition to being well suited for the removal or detachment of pacing leads from a patient, embodiments of the present invention are well suited for detaching or removing any of a variety of objects from a patient, such as catheters, wires, implants, or other foreign bodies. Such objects may be disposed in veins, arteries, or any body lumen, cavity, or tissue.

Embodiments of the invention have now been described in detail. However, it will be appreciated that the invention may be carried out in ways other than those illustrated in the aforesaid discussion, and that certain changes and modifications may be practiced within the scope of the appended claims. Accordingly, the scope of this invention is not intended to be limited by those specific examples, but rather is to be accorded the scope represented in the following claims.

What is claimed is:

1. A system for separating an object from a patient tissue, comprising:
   a sheath having a proximal end and a distal end; and
   a cylindrical separator coupled with the distal end of the sheath, the separator having an internal lumen, an upper side, a lower side, a proximal end, and a distal end having a separating mechanism,
   wherein the internal lumen of the separator defines a central longitudinal axis and is sized to receive the object,
   wherein the distal end of the separating mechanism comprises a distal face oriented at an acute angle relative to the central longitudinal axis and extending in a planar fashion from the upper side to the lower side such that an entire diameter of the internal lumen is open at the distal face,
   wherein the distal face comprises an abrasive material,
   wherein the distal face is configured such that whereupon being pressed against patient tissue, the separating mechanism does not separate patient tissue, and whereupon rotating the separating mechanism, the separating mechanism separates patient tissue.

2. The system according to claim 1, wherein the abrasive material comprises a member selected from the group consisting of a diamond, an aluminum carbide, and a silica carbide.

3. The system according to claim 2, wherein the acute angle is within a range from about 30 degrees to about 85 degrees.

4. The system according to claim 3, wherein the member is a first member, and wherein the separator comprises a second member selected from the group consisting of a cutting member, a dilating member, and a stripping member.

5. The system according to claim 2, wherein the member is a first member, and wherein the separator comprises a second member selected from the group consisting of a cutting member, a dilating member, and a stripping member.

6. The system according to claim 1, wherein the acute angle is within a range from about 30 degrees to about 85 degrees.

7. The system according to claim 6, wherein the separator comprises a member selected from the group consisting of a cutting member, a dilating member, and a stripping member.

8. The system according to claim 1, wherein the separator comprises a member selected from the group consisting of a cutting member, a dilating member, and a stripping member.

9. A system for separating an object from a patient tissue, comprising:

sheath having a proximal end and a distal end; and a cylindrical separator coupled with the distal end of the sheath, the separator having an internal lumen sized to receive the object, a proximal end, a distal end, and a longitudinal axis, wherein the distal end has a rim, wherein the rim comprises a first portion and a second portion, wherein the distal end comprises a distal face disposed at an acute angle relative to the longitudinal axis such that an entire diameter of the internal lumen is open at the distal face, wherein the first portion comprises a separating mechanism and the second portion comprises a blunt edge, wherein the separating mechanism is configured such that whereupon the distal end being pressed against patient tissue, the second portion does not separate patient tissue, and whereupon rotating the separating mechanism, the first portion separates patient tissue.

10. The system according to claim 9, wherein the separating mechanism comprises abrasive material.

11. The system according to claim 9, wherein the separating mechanism comprises a blade.

* * * * *